(12) United States Patent
Chen et al.

(10) Patent No.: US 11,091,494 B2
(45) Date of Patent: Aug. 17, 2021

(54) CRYSTAL FORM OF ACALABRUTINIB AND PREPARATION METHOD AND USE THEREOF

(71) Applicant: Crystal Pharmaceutical (Suzhou) Co., Ltd., Jiangsu (CN)

(72) Inventors: Minhua Chen, Suzhou (CN); Yanfeng Zhang, Suzhou (CN); Yuan Liu, Suzhou (CN); Jianming Wang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/959,700

(22) PCT Filed: Nov. 20, 2018

(86) PCT No.: PCT/CN2018/116288
§ 371 (c)(1),
(2) Date: Jul. 2, 2020

(87) PCT Pub. No.: WO2019/134455
PCT Pub. Date: Jul. 11, 2019

(65) Prior Publication Data
US 2020/0347069 A1    Nov. 5, 2020

(30) Foreign Application Priority Data
Jan. 5, 2018    (CN) .......................... 201810011409.1

(51) Int. Cl.
*C07D 487/04*    (2006.01)
(52) U.S. Cl.
CPC ........ *C07D 487/04* (2013.01); *C07B 2200/13* (2013.01)
(58) Field of Classification Search
None
See application file for complete search history.

(56) References Cited

U.S. PATENT DOCUMENTS

2017/0035881 A1    2/2017    Lannutti et al.

FOREIGN PATENT DOCUMENTS

| CN | 107056786 A | 8/2017 |
|---|---|---|
| CN | 107522701 A | 12/2017 |
| WO | WO-2013/010868 A1 | 1/2013 |
| WO | WO-2017/002095 A1 | 1/2017 |
| WO | 2018/064797 A1 | 4/2018 |

OTHER PUBLICATIONS

International Search Report and Written Opinion for Application No. PCT/CN2018/116288, dated Feb. 26, 2019, 10 pages.
U.S. Appl. No. 17/050,329, filed Oct. 23, 2020, Pending.
International Search Report and Written Opinion for Application No. PCT/CN2019/076944, dated Jun. 5, 2019, 8 pages.

*Primary Examiner* — Brian J Davis
(74) *Attorney, Agent, or Firm* — McCarter & English, LLP; Steven G. Davis; Wei Song

(57) ABSTRACT

The present disclosure relates to novel crystalline forms of acalabrutinib and processes for preparation thereof. The present disclosure also relates to pharmaceutical compositions containing acalabrutinib, use of acalabrutinib for preparing Bruton's tyrosine kinase inhibitor drug, and use of acalabrutinib for preparing drugs treating mantle cell lymphoma. The crystalline forms of the present disclosure have one or more improved properties compared with prior art, and have significant value for future drug optimization and development.

Compound I

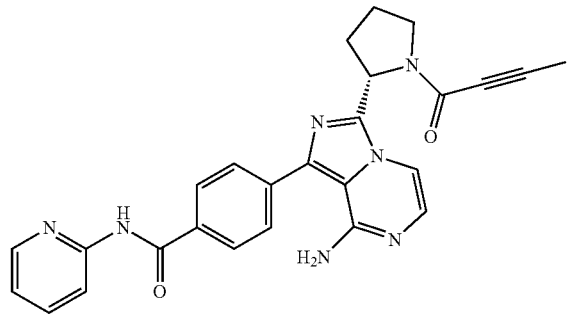

14 Claims, 40 Drawing Sheets

CRYSTAL FORM OF ACALABRUTINIB AND PREPARATION METHOD AND USE THEREOF

CROSS-REFERENCE TO RELATED APPLICATIONS

This application is a U.S. national stage filing, under 35 U.S.C. § 371(c), of International Application No. PCT/CN2018/116288, filed on Nov. 20, 2018, which claims priority to Chinese Patent Application No. 201810011409.1, filed on Jan. 5, 2018. The entire contents of each of the aforementioned applications are incorporated herein by reference.

TECHNICAL FIELD

The present disclosure relates to the field of pharmaceutical chemistry, particularly relates to novel crystalline forms of acalabrutinib, processes for preparation and use thereof.

BACKGROUND

Mantle Cell Lymphoma is a type of non-Hodgkin's lymphoma and is a hard-to-treat lymphoma. BTK is a member of the Tec family of tyrosine kinases and has been shown as a key regulator of early B cell development as well as activation and survival of mature B cells. BTK has been reported to play a role in apoptosis, and thus BTK inhibitors are useful in the treatment of certain B-cell lymphomas and leukemias.

Acalabrutinib is a second-generation BTK inhibitor with higher selectivity and lower side effects compared with the first-generation BTK inhibitor ibrutinib. The approval of acalabrutinib provides a new treatment option for patients with relapsed drug-resistant mantle cell lymphoma. Acalabrutinib was developed by Acerta and approved in the US in October 2017. The chemical name of Acalabrutinib is (S)-4-(8-amino-3-(1-(but-2-ynoyl)pyrrolidin-2-yl)imidazo[1,5-a]pyrazin-1-yl)-N-(pyridin-2-yl)benzamide (hereinafter referred to as "compound I"), and the structure is shown as follows:

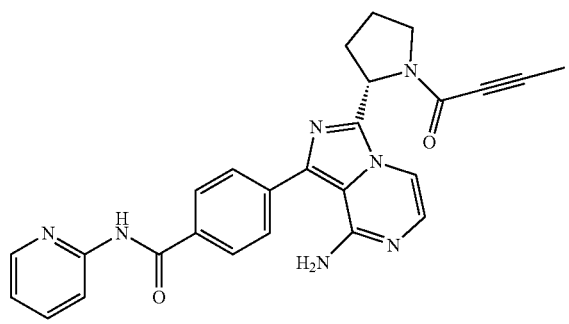

Compound I

Crystalline forms are different solids formed by different arrangement of compound molecules in the lattice space. Polymorphism is the ability of a compound to exist in two or more than two crystalline forms.

Different crystalline forms of the same drug substance may have different in vivo dissolution and absorption, which will further affect drug's clinical efficacy and safety to some extent. In particular, for poorly soluble oral drugs, the above effects of the crystalline form will be greater. Therefore, in the development of solid oral formulations, the study of crystalline forms facilitates the selection of a clinically and therapeutically meaningful, stable and controllable crystalline form. Drug polymorphism is an important part of drug research, testing and supervision, and an important part of drug quality control.

WO2017002095A1 disclosed eight crystalline forms of acalabrutinib. It disclosed that crystalline form I is an anhydrate. Crystalline form II is a trihydrate with poor flowability and non-uniform particle size. Water content in crystalline form II varies in different conditions with a highest water content of 10%. Crystalline form III is an unstable dihydrate. Water content in crystalline form III varies in different conditions with a highest water content of 8%. Crystalline form IV and crystalline form V are unstable anhydrates and were obtained by dehydration at low RH (relative humidity) and elevated temperature, respectively. Crystalline form VI and crystalline form VII are methanol solvates; crystalline form VIII is an acetic acid solvate. Therefore, it is essential to perform polymorph screening to find crystalline forms that can be used for preparing drug product, making the developed crystalline form more suitable for industrial production.

The present disclosure provides ethyl L-lactate solvate crystalline form A, glycerol solvate crystalline form D, (S)-1,2-propanediol solvate crystalline form F, (R)-1,2-propanediol solvate crystalline form G and (R)-1,2-propanediol solvate crystalline form CS15 of acalabrutinib, which have advantages in at least one aspect of stability, melting point, solubility, in vitro and in vivo dissolution, hygroscopicity, bioavailability, adhesiveness, compressibility, flowability, processability, purification ability, formulation development etc. In particular, these forms have low toxic process solvent, simple preparation process, good repeatability, remarkable purification effect, high dissolution rate, low hygroscopicity, better flowability, better compressibility and better adhesiveness, which provides new and better choices for preparation of drug product containing acalabrutinib and has significant values for future drug development.

SUMMARY

The main objective of the present disclosure is to provide novel crystalline forms of acalabrutinib, processes for preparation and use thereof.

According to the objective of the present disclosure, ethyl L-lactate solvate crystalline form A of compound I is provided (hereinafter referred to as Form A).

According to one aspect of the present disclosure, the X-ray powder diffraction pattern of Form A shows characteristic peaks at 2theta values of 5.7°±0.2°, 17.4°±0.2° and 18.2°±0.2° using CuKα radiation.

Furthermore, the X-ray powder diffraction pattern of Form A shows one or two or three characteristic peaks at 2theta values of 8.5°±0.2°, 13.9°±0.2° and 24.8°±0.2°; Preferably, the X-ray powder diffraction pattern of Form A shows characteristic peaks at 2theta values of 8.5°±0.2°, 13.9°±0.2° and 24.8°±0.2°.

Furthermore, the X-ray powder diffraction pattern of Form A shows one or two or three characteristic peaks at 2 theta values of 19.2°±0.2°, 22.9°±0.2° and 15.1°±0.2°; Preferably, the X-ray powder diffraction pattern of Form A shows characteristic peaks at 2theta values of 19.2°±0.2°, 22.9°±0.2° and 15.1°±0.2°.

According to another aspect of the present disclosure, the X-ray powder diffraction pattern of Form A shows three or four or five or six or seven or eight or nine characteristic peaks at 2theta values of 5.7°±0.2°, 17.4°±0.2°, 18.2°±0.2°, 8.5°±0.2°, 13.9°±0.2°, 24.8°±0.2°, 19.2°±0.2°, 22.9°±0.2° and 15.1°±0.2° using CuKα radiation.

Without any limitation being implied, the X-ray powder diffraction pattern of Form A is substantially as depicted in FIG. 1.

According to the objective of the present disclosure, a process for preparing Form A is also provided. The process comprises:

Suspending acalabrutinib free base in ethyl L-lactate or a solvent containing ethyl L-lactate, reacting for 1-3 days at 5-60° C. to obtain a solid.

Where:

Said reaction temperature is preferably 40-50° C.;

Said reaction time is preferably 24 hours.

Form A of the present disclosure has the following advantages:

(1) Form A of the present disclosure has good physical stability. Crystalline state of Form A doesn't change and chemical purity remains substantially unchanged for at least 2 months when stored under the condition of 25° C./60% RH (Relative Humidity) in open and closed dishes. These results show that drug substance Form A of the present disclosure has good long-term stability, which is beneficial for the storage of drug products. Meanwhile, the crystalline state of Form A doesn't change for at least 2 months when stored under the condition of 40° C./75% RH in open and closed dishes. These results show that drug substance Form A of the present disclosure has good accelerated stability, which is beneficial for the storage of drug products under special conditions, such as the tropical regions.

Crystalline transformation can lead to changes in the absorption of a drug, and cause toxicity and side effects. Form A has good physical stability, ensuring consistent and controllable quality of the drug substance and drug product, minimizing the increase of the drug toxicity due to crystal transformation, and ensuring the effectiveness of the drug.

(2) Compared with prior art, Form A of the present disclosure has better dissolution rate. In pH 2.5 HCl/NaCl solution, the intrinsic dissolution rate of Form A drug substance is 1.2 times higher than that of prior art Form I in WO2017002095A1.

Drug with different crystalline forms may lead to different in vivo dissolution rates, which directly affects drug's in vivo absorption, distribution, excretion, metabolism, and finally leads to difference in clinical efficacy due to different bioavailability. Dissolution rate is an important prerequisite for drug absorption, and high dissolution rate is beneficial for the drug to achieve peak concentration in plasma quickly after administration, thus ensuring rapid drug action.

(3) Form A of the present disclosure has good purification effect. The purity is significantly increased after the raw material is converted into Form A. In a specific embodiment, the purity of the raw material used in the present disclosure is 98.93%. The purity of Form A made from the raw material is 99.63%, and the purity is increased by 0.70%.

Chemical purity of a drug is of great significance for ensuring drug efficacy and safety, preventing the occurrence of adverse effects. Impurities in drugs are the main factors affecting purity. If the drug contains impurities higher than limit, its physicochemical properties and drug appearance may change, and the stability will be affected. The increase of impurities will lead to significantly lowered active ingredient content or reduced drug activity, and will also lead to significantly increased toxicity and side effects of the drug products. Crystalline forms with good purification effect are excellent in removing impurities in the crystallization process, thus drug substances with high purity can be obtained through crystallization, which effectively overcome the disadvantages of poor stability, poor efficacy and high toxicity caused by the low purity drug substances.

(4) Form A of the present disclosure has low hygroscopicity. The test results show that Form A is slightly hygroscopic with a weight gain of 0.99% at 80% RH.

Hygroscopicity affects the drug stability, flowability and uniformity during production process, thereby affecting the quality of the drug product. Moreover, hygroscopicity affects the production, post-process and storage of drug. The crystalline form with low hygroscopicity is not demanding on the environment, which reduces the cost of production, storage and quality control, and has strong economic value.

Furthermore, Form A of the present disclosure also has the following advantages:

(1) Compared with prior art, Form A of the present disclosure has better compressibility. Failure in harness/friability test and tablet crack issue can be avoided due to better compressibility, making the preparation process more controllable, improving product appearance and product quality. Better compressibility can increase the compression rate, thus further increases the efficiency of process and reduces the cost of compressibility improving excipients.

(2) Compared with prior art, Form A of the present disclosure shows superior adhesiveness. Adhesiveness evaluation results indicate that adhesion quantity of Form A is remarkably lower than that of prior art forms. Due to superior adhesiveness of Form A, adhesion to roller and tooling during dry-granulation and compression process can be reduced, which is also beneficial to improve product appearance and weight variation. In addition, superior adhesiveness of Form A can reduce the agglomeration of drug substance, which is beneficial to the dispersion of drug substance and reduce the adhesion between drug substance and instruments, and improves the blend uniformity and content uniformity of drug product.

(3) Form A of the present disclosure has better flowability. Better flowability can effectively improve the production speed and efficiency of tableting and filling, increase the manufacturing efficiency. Better flowability of Form A ensures the blend uniformity and content uniformity of the drug product, reduces the weight variation in the drug product and improves product quality.

According to the objective of the present disclosure, glycerol solvate crystalline form D of compound I is provided (hereinafter referred to as Form D).

According to one aspect of the present disclosure, the X-ray powder diffraction pattern of Form D shows characteristic peaks at 2theta values of 14.2°±0.2°, 6.7°±0.2° and 13.4°±0.2° using CuKα radiation.

Furthermore, the X-ray powder diffraction pattern of Form D shows one or two or three characteristic peaks at 2theta values of 16.2°±0.2°, 11.0°±0.2° and 9.6°±0.2°. Preferably, the X-ray powder diffraction pattern of Form CSI shows characteristic peaks at 2theta values of 16.2°±0.2°, 11.0°±0.2° and 9.6°±0.2°.

Furthermore, the X-ray powder diffraction pattern of Form D shows one or two or three characteristic peaks at 2theta values of 8.1°±0.2°, 24.3°±0.2° and 20.3°±0.2°. Preferably, the X-ray powder diffraction pattern of Form D shows characteristic peaks at 2theta values of 8.1°±0.2°, 24.3°±0.2° and 20.3°±0.2°.

According to another aspect of the present disclosure, the X-ray powder diffraction pattern of Form D shows three or four or five or six or seven or eight or nine characteristic peaks at 2theta values of 14.2°±0.2°, 6.7°±0.2°, 13.4°±0.2°, 16.2°±0.2°, 11.0°±0.2°, 9.6°±0.2°, 8.1°±0.2°, 24.3°±0.2° and 20.3°±0.2° using CuKα radiation.

Without any limitation being implied, the X-ray powder diffraction pattern of Form D is substantially as depicted in FIG. 9.

According to the objective of the present disclosure, a process for preparing Form D is also provided. The process comprises:

Suspending Acalabrutinib free base in glycerol or a solvent containing glycerol. Then, putting it under 20-80° C. and reacting for 10-72 hours to obtain a solid.

Where:

Said reaction temperature is preferably 50-60° C.;

Said reaction time is preferably 24 hours.

Form D of the present disclosure has the following advantages:

(1) Form D of the present disclosure has good physical stability. Crystalline state of Form D doesn't change and chemical purity remains substantially unchanged for at least 2 months when stored under the condition of 25° C./60% RH in open and closed dishes. These results show that drug substance Form D of the present disclosure has good long-term stability, which is beneficial for the storage of drug products. Meanwhile, the crystalline state of Form D doesn't change for at least 2 months when stored under the condition of 40° C./75% RH in closed dish. The result show that drug substance Form D of the present disclosure has good accelerated stability, which is beneficial for the storage of drug products under special conditions, for example the tropical regions.

Crystalline transformation can lead to changes in the absorption of a drug, and cause toxicity and side effects. Form D has good physical stability, ensuring consistent and controllable quality of the drug substance and drug product, minimizing the increase of the drug toxicity due to crystal transformation, and ensuring the effectiveness of the drug.

(2) Form D of the present disclosure has good purification effect. The purity is significantly increased after the raw material is converted into Form D. In a specific embodiment, the purity of the raw material used in the present disclosure is 98.93%. The purity of Form D made from the raw material is 99.49%, and the purity is increased by 0.56%.

Chemical purity of a drug is of great significance for ensuring drug efficacy and safety, preventing the occurrence of adverse effects. Impurities in drugs are the main factors affecting purity. If the drug contains impurities higher than limit, its physicochemical properties and drug appearance may change, and the stability will be affected. The increase in impurities will lead to significantly lowered active ingredient content or reduced drug activity, and will also lead to significantly increased toxicity and side effects of the drug products. Crystalline forms with good purification effect are excellent in removing impurities in the crystallization process, thus drug substances with high purity can be obtained through crystallization, which effectively overcome the disadvantages of poor stability, poor efficacy and high toxicity caused by the low purity drug substances.

(3) Compared with prior art, Form D of the present disclosure has better dissolution rate. In pH 2.5 HCl/NaCl solution, the intrinsic dissolution rate of Form D drug substance is 1.1 times higher than that of prior art Form I in WO2017002095A1.

Drug with different crystalline forms may lead to different in vivo dissolution rates, which directly affects drug's in vivo absorption, distribution, excretion, metabolism, and finally leads to difference in clinical efficacy due to different bioavailability. Dissolution rate is an important prerequisite for drug absorption, and high dissolution rate is beneficial for the drug to achieve peak concentration in plasma quickly after administration, thus ensuring rapid drug action.

Furthermore, Form D of the present disclosure also has the following advantages:

Compared with prior art, Form D of the present disclosure has better compressibility. Failure in hardness/friability test and tablet crack issue can be avoided due to better compressibility, making the preparation process more reliable, improving product appearance and product quality. Better compressibility can increase the compression rate, thus further increases the efficiency of process and reduces the cost of compressibility improving excipients.

According to the objective of the present disclosure, (S)-1,2-propanediol solvate crystalline form F of compound I is provided (hereinafter referred to as Form F).

According to one aspect of the present disclosure, the X-ray powder diffraction pattern of Form F shows characteristic peaks at 2theta values of 16.1°±0.2°, 24.3°±0.2° and 12.4°±0.2° using CuKα radiation.

Furthermore, the X-ray powder diffraction pattern of Form F shows one or two or three characteristic peaks at 2theta values of 10.0°±0.2°, 18.0°±0.2° and 13.2°±0.2°. Preferably, the X-ray powder diffraction pattern of Form F shows characteristic peaks at 2theta values of 10.0°±0.2°, 18.0°±0.2° and 13.2°±0.2°.

Furthermore, the X-ray powder diffraction pattern of Form F shows one or two or three characteristic peaks at 2theta values of 8.1°±0.2°, 14.5°±0.2° and 18.9°±0.2°. Preferably, the X-ray powder diffraction pattern of Form F shows characteristic peaks at 2theta values of 8.1°±0.2°, 14.5°±0.2° and 18.9°±0.2°.

According to another aspect of the present disclosure, the X-ray powder diffraction pattern of Form F shows three or four or five or six or seven or eight or nine or ten characteristic peaks at 2theta values of 16.1°±0.2°, 24.3°±0.2°, 12.4°±0.2°, 10.0°±0.2°, 18.0°±0.2°, 13.2°±0.2°, 8.1°±0.2°, 14.5°±0.2°, 18.9°±0.2° and 6.6°±0.2° using CuKα radiation.

Without any limitation being implied, the X-ray powder diffraction pattern of Form F is substantially as depicted in FIG. 13.

According to the objective of the present disclosure, a process for preparing Form F is also provided. The process comprises:

Suspending acalabrutinib free base in (S)-1,2-propanediol or a solvent containing (S)-1,2-propanediol, reacting for 10-72 hours at 5-60° C. to obtain a solid.

Where:

Said reaction temperature is preferably from room temperature to 50° C.;

Said reaction time is preferably 24 hours.

Form F of the present disclosure has the following advantages:

(1) Form F of the present disclosure has good physical stability. Crystalline state of Form F doesn't change and chemical purity remains substantially unchanged for at least 2 months when stored under the condition of 25° C./60% RH in open and closed dishes. These results show that drug substance Form F of the present disclosure has good long-term stability, which is beneficial for the storage of drug products. Meanwhile, the crystalline state of Form F doesn't change for at least 2 months when stored under the condition of 40° C./75% RH in open and closed dishes.

Good stability is of great importance to the drug development. There are storage, transportation and formulation processes from drug substance to drug product. Most common stress conditions encountered in these processes are high temperature and high humidity. The conditions are caused by the collision of drug substance in storage and transportation, the wet granulation process in drug production, the seasonal and regional climate differences, and weather factors. High temperature and high humidity are the most common stress conditions. Prior art solid partially converted to a crystalline form after being stored under high temperature and high humidity conditions, while the crystalline forms of the present disclosure didn't change.

Crystalline transformation can lead to changes in the absorption of a drug, and cause toxicity and side effects. Form F has good physical stability, ensuring consistent and controllable quality of the drug substance and drug product, minimizing the increase of the drug toxicity due to crystal transformation, and ensuring the effectiveness of the drug.

(2) Compared with prior art, Form F of the present disclosure has better dissolution rate. In pH 2.5 HCl/NaCl solution, the intrinsic dissolution rate of Form F drug substance is 1.3 times higher than that of prior art Form I in WO2017002095A1.

Drug with different crystalline forms may lead to different in vivo dissolution rates, which directly affects drug's in vivo absorption, distribution, excretion, metabolism, and finally leads to difference in clinical efficacy due to different bioavailability. Dissolution rate is an important prerequisite for drug absorption, and high dissolution rate is beneficial for the drug to achieve peak concentration in plasma quickly after administration, thus ensuring rapid drug action.

(3) Form F of the present disclosure has good purification effect. The purity is significantly increased after the raw material is converted into Form F. In a specific embodiment, the purity of the raw material used in the present disclosure is 98.93%. The purity of Form F made from the raw material is 99.80%, and the purity is increased by 0.87%.

Chemical purity of a drug is of great significance for ensuring drug efficacy and safety, preventing the occurrence of adverse effects. Impurities in drugs are the main factors affecting purity. If the drug contains impurities higher than limit, its physicochemical properties and drug appearance may change, and the stability will be affected. The increase in impurities will lead to significantly lowered active ingredient content or reduced drug activity, and will also lead to significantly increased toxicity and side effects of the drug products. Crystalline forms with good purification effect are excellent in removing impurities in the crystallization process, thus drug substances with high purity can be obtained through crystallization, which effectively overcomes the disadvantages of poor stability, poor efficacy and high toxicity caused by the low purity drug substances.

(4) Form F of the present disclosure has low hygroscopicity. The test results show that Form F is non hygroscopic or almost non hygroscopic with a weight gain of 0.09% at 80% RH.

Hygroscopicity affects the drug stability, flowability and uniformity during production process, thereby affecting the quality of the drug product. Moreover, hygroscopicity affects the production, post-process and storage of drug. The crystalline form with low hygroscopicity is not demanding on the environment, which reduces the cost of storage and quality control, and has strong economic value.

Furthermore, Form F of the present disclosure also has the following advantages:

(1) Compared with prior art, Form F of the present disclosure has better compressibility. Failure in hardness/friability test and tablet crack issue can be avoided due to better compressibility, making the preparation process more controllable, improving product appearance and product quality. Better compressibility can increase the compression rate, thus further increases the efficiency of process and reduces the cost of compressibility improving excipients.

(2) Compared with prior art, Form F of the present disclosure shows superior adhesiveness. Adhesiveness evaluation results indicate that adhesion quantity of Form F is remarkably lower than that of prior art forms. Due to superior adhesiveness of Form F, adhesion to roller and tooling during dry-granulation and compression process can be reduced, which is also beneficial to improve product appearance and weight variation. In addition, superior adhesiveness of Form F can reduce the agglomeration of drug substance, which is beneficial to the dispersion of drug substance and reduce the adhesion between drug substance and instruments, and improves the blend uniformity and content uniformity of drug product.

(3) Form F of the present disclosure has better flowability. Better flowability can effectively improve the production speed and efficiency of tableting and filling, increase the manufacturing efficiency. Better flowability of Form F ensures the blend uniformity and content uniformity of the drug product, reduces the weight variation in the drug product and improves product quality.

According to the objective of the present disclosure, (R)-1,2-propanediol solvate crystalline form G of compound I is provided (hereinafter referred to as Form G).

According to one aspect of the present disclosure, the X-ray powder diffraction pattern of Form G shows characteristic peaks at 2theta values of 5.1°±0.2°, 12.2°±0.2° and 13.5°±0.2° using CuKα radiation.

Furthermore, the X-ray powder diffraction pattern of Form G shows one or two or three characteristic peaks at 2theta values of 15.6°±0.2°, 17.0°±0.2° and 6.6°±0.2°. Preferably, the X-ray powder diffraction pattern of Form G shows characteristic peaks at 2theta values of 15.6°±0.2°, 17.0°±0.2° and 6.6°±0.2°.

Furthermore, the X-ray powder diffraction pattern of Form G shows one or two or three characteristic peaks at 2theta values of 23.0°±0.2°, 17.7°±0.2° and 21.3°±0.2°. Preferably, the X-ray powder diffraction pattern of Form G shows characteristic peaks at 2theta values of 23.0°±0.2°, 17.7°±0.2° and 21.3°±0.2°.

According to another aspect of the present disclosure, the X-ray powder diffraction pattern of Form G shows three or four or five or six or seven or eight or nine characteristic peaks at 2theta values of 5.1°±0.2°, 12.2°±0.2°, 13.5°±0.2°, 15.6°±0.2°, 17.0°±0.2°, 6.6°±0.2°, 23.0°±0.2°, 17.7°±0.2° and 21.3°±0.2° using CuKα radiation.

Without any limitation being implied, the X-ray powder diffraction pattern of Form G is substantially as depicted in FIG. 17.

According to the objective of the present disclosure, a process for preparing Form G is also provided. The process comprises:

Suspending acalabrutinib free base in (R)-1,2-propanediol or a solvent containing (R)-1,2-propanediol, reacting for 10-48 hours at 5-60° C. to obtain a solid.

Where:

Said reaction temperature is preferably room temperature;

Said reaction time is preferably 24 hours.

Form G of the present disclosure has the following advantages:

(1) Form G of the present disclosure has good physical stability. Crystalline state of Form G doesn't change and chemical purity remains substantially unchanged for at least 2 months when stored under the condition of 25° C./60% RH in closed dish. The result show that drug substance Form G of the present disclosure has good long-term stability, which is beneficial for the storage of drug products.

Crystalline transformation can lead to changes in the absorption of a drug, and cause toxicity and side effects. Form G has good physical stability, ensuring consistent and controllable quality of the drug substance and drug product, minimizing the increase of the drug toxicity due to crystal transformation, and ensuring the effectiveness of the drug.

(2) Compared with prior art, Form G of the present disclosure has better dissolution rate. In pH 2.5 HCl/NaCl solution, the intrinsic dissolution rate of Form G drug substance is 1.2 times higher than that of prior art Form I in WO2017002095A1.

Drug with different crystalline forms may lead to different in vivo dissolution rates, which directly affects drug's in vivo absorption, distribution, excretion, metabolism, and finally leads to difference in clinical efficacy due to different bioavailability. Dissolution rate is an important prerequisite for drug absorption, and high dissolution rate is beneficial for the drug to achieve peak concentration in plasma quickly after administration, thus ensuring rapid drug action.

(3) Form G of the present disclosure has good purification effect. The purity is significantly increased after the raw material is converted into Form G. In a specific embodiment, the purity of the raw material used in the present disclosure is 98.93%. The purity of Form G made from the raw material is 99.86%, and the purity is increased by 0.93%.

Chemical purity of a drug is of great significance for ensuring drug efficacy and safety, preventing the occurrence of adverse effects. Impurities in drugs are the main factors affecting purity. If the drug contains impurities higher than limit, its physicochemical properties and drug appearance may change, and the stability will be affected. The increase in impurities will lead to significantly lowered active ingredient content or reduced drug activity, and will also lead to significantly increased toxicity and side effects of the drug products. Crystalline forms with good purification effect are excellent in removing impurities in the crystallization process, thus drug substances with high purity can be obtained through crystallization, which effectively overcome the disadvantages of poor stability, poor efficacy and high toxicity caused by the low purity drug substances.

Furthermore, Form G of the present disclosure also has the following advantages:

(1) Compared with prior art, Form G of the present disclosure has better compressibility. Failure in hardness/friability test and tablet crack issue can be avoided due to better compressibility, making the preparation process more controllable, improving product appearance and product quality. Better compressibility can increase the compression rate, thus further increases the efficiency of process and reduces the cost of compressibility improving excipients.

(2) Compared with prior art, Form G of the present disclosure shows superior adhesiveness. Adhesiveness evaluation results indicate that adhesion quantity of Form G is remarkably lower than that of prior art forms. Due to superior adhesiveness of Form G, adhesion to roller and tooling during dry-granulation and compression process can be reduced, which is also beneficial to improve product appearance and weight variation. In addition, superior adhesiveness of Form G can reduce the agglomeration of drug substance, which is beneficial to the dispersion of drug substance and reduce the adhesion between drug substance and instruments, and improve the blend uniformity and content uniformity of drug product.

(3) Form G of the present disclosure has better flowability. Better flowability can effectively improve the production speed and efficiency of tableting and filling, increase the manufacturing efficiency. Better flowability of Form G ensures the blend uniformity and content uniformity of the drug product, reduces the weight variation in the drug product and improves product quality.

According to the objective of the present disclosure, (R)-1,2-propanediol solvate crystalline form CS15 of compound I is provided (hereinafter referred to as Form CS15).

According to one aspect of the present disclosure, the X-ray powder diffraction pattern of Form CS15 shows characteristic peaks at 2theta values of 8.6°±0.2°, 9.3°±0.2° and 13.6°±0.2° using CuKα radiation.

Furthermore, the X-ray powder diffraction pattern of Form CS15 shows one or two or three or four characteristic peaks at 2theta values of 8.0°±0.2°, 14.3°±0.2°, 17.4°±0.2° and 19.2°±0.2°. Preferably, the X-ray powder diffraction pattern of Form CS15 shows characteristic peaks at 2theta values of 8.0°±0.2°, 14.3°±0.2°, 17.4°±0.2° and 19.2°±0.2°.

According to another aspect of the present disclosure, the X-ray powder diffraction pattern of Form CS15 shows three or four or five or six or seven or eight or nine or ten characteristic peaks at 2theta values of 8.6°±0.2°, 9.3°±0.2°, 13.6°±0.2°, 8.0°±0.2°, 14.3°±0.2°, 17.4°±0.2°, 19.2°±0.2°, 20.2°±0.2°, 22.2°±0.2° and 22.9°±0.2° using CuKα radiation.

Without any limitation being implied, the X-ray powder diffraction pattern of Form CS15 is substantially as depicted in FIG. 21.

According to the objective of the present disclosure, a process for preparing Form CS15 is also provided. The process comprises:

Suspending Acalabrutinib free base in (R)-1,2-propanediol. Putting it under 5-60° C. and reacting for 10-48 hours to obtain samples. Then, suspending the obtained samples it in a nitrile, stirring at −20-5° C. for 1-7 days to obtain a solid; or Suspending acalabrutinib free base in a solvent mixture of (R)-1,2-propanediol and a nitrile, reacting for 10-48 hours at 5-60° C. to obtain a solid.

Where:

Said reaction temperature is preferably room temperature;

Said reaction time is preferably 24 hours.

Form CS15 of the present disclosure has the following advantages:

(1) Form CS15 of the present disclosure has good physical stability. Crystalline state of Form CS15 doesn't change and chemical purity remains substantially unchanged for at least 2 months when stored under the condition of 25° C./60% RH in open and closed dishes. The result show that drug substance Form CS15 of the present disclosure has good long-term stability, which is beneficial for the storage of drug products.

Crystalline transformation can lead to changes in the absorption of a drug, and cause toxicity and side effects. Form CS15 has good physical stability, ensuring consistent and controllable quality of the drug substance and drug product, minimizing the increase of the drug toxicity due to crystal transformation, and ensuring the effectiveness of the drug.

(2) Compared with prior art, Form CS15 of the present disclosure has better dissolution rate. In pH 2.5 HCl/NaCl solution, the intrinsic dissolution rate of Form CS15 drug substance is 1.6 times higher than that of prior art Form I in WO2017002095A1.

Drug with different crystalline forms may lead to different in vivo dissolution rates, which directly affects drug's in vivo absorption, distribution, excretion, metabolism, and finally leads to difference in clinical efficacy due to different bioavailability. Dissolution rate is an important prerequisite for drug absorption, and high dissolution rate is beneficial for the drug to achieve peak concentration in plasma quickly after administration, thus ensuring rapid drug action.

(3) Form CS15 of the present disclosure has good purification effect. The purity is significantly increased after the raw material is converted into Form G. In a specific embodiment, the purity of the raw material used in the present disclosure is 99.20%. The purity of Form CS15 made from the raw material is 99.83%, and the purity is increased by 0.63%.

Chemical purity of a drug is of great significance for ensuring drug efficacy and safety, preventing the occurrence of adverse effects. Impurities in drugs are the main factors affecting purity. If the drug contains impurities higher than limit, its physicochemical properties and drug appearance may change, and the stability will be affected. The increase in impurities will lead to significantly lowered active ingredient content or reduced drug activity, and will also lead to significantly increased toxicity and side effects of the drug products. Crystalline forms with good purification effect are excellent in removing impurities in the crystallization process, thus drug substances with high purity can be obtained through crystallization, which effectively overcomes the disadvantages of poor stability, poor efficacy and high toxicity caused by the low purity drug substances.

(4) Form CS15 of the present disclosure has low hygroscopicity. The test results show that Form CS15 is slightly hygroscopic with a weight gain of 1.78% at 80% RH.

Hygroscopicity affects the drug stability, flowability and uniformity during production process, thereby affecting the quality of the drug product. Moreover, hygroscopicity affects the production, post-process and storage of drug. The crystalline form with low hygroscopicity is not demanding on the environment, which reduces the cost of storage and quality control, and has strong economic value.

Furthermore, Form CS15 of the present disclosure also has the following advantages:

Compared with prior art, Form CS15 of the present disclosure has better compressibility. Failure in hardness/friability test and tablet crack issue can be avoided due to better compressibility, making the preparation process more controllable, improving product appearance and product quality. Better compressibility can increase the compression rate, thus further increases the efficiency of process and reduces the cost of compressibility improving excipients.

According to the objective of the present disclosure, ethylene glycol solvate crystalline form B of compound I is provided (hereinafter referred to as Form B).

The X-ray powder diffraction pattern of Form B shows one or more characteristic peaks at 2theta values of 7.1°±0.2°, 5.1°±0.2°, 14.1°±0.2°, 13.3°±0.2°, 11.8°±0.2°, 21.6°±0.2°, 18.1°±0.2°, 11.3°±0.2° and 8.0°±0.2° using CuKα radiation.

According to the objective of the present disclosure, a process for preparing Form B is also provided. The process comprises:

Dissolving acalabrutinib free base into ethylene glycol, placing the solution into a closed environment with ester vapor and reacting for 1-7 days at 5-40° C. to obtain a solid.

Where:
Said ester is preferably isopropyl acetate;
Said reaction temperature is preferably room temperature;
Said reaction time is preferably 3 days.

According to the objective of the present disclosure, a pharmaceutical composition is provided, said pharmaceutical composition comprises a therapeutically effective amount of Form A, Form D, Form F, Form G and Form CS15 or combinations thereof and pharmaceutically acceptable carriers, diluents or excipients.

Furthermore, the use of Form A, Form D, Form F, Form G and Form CS15 of the present disclosure or combinations thereof for preparing Bruton's tyrosine kinase inhibitor drug was provided.

Furthermore, the use of Form A, Form D, Form F, Form G and Form CS15 of the present disclosure or combinations thereof for preparing drugs treating mantle cell lymphoma was provided.

In the present disclosure "room temperature" is not a specific temperature, but a temperature range of 10-30° C.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sample preparation and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form A, Form D, Form F, Form G and Form CS15 of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the number and the number range should not be understood as the number or number range themselves only. It should be understood by those skilled in the art that the specific number can be shifted at specific technical environment without departing from the spirit and principle of the present disclosure. In the present disclosure, the shift ranges expected by those skilled in the art is represented by the term "about".

DETAILED DESCRIPTION

The parameters of the test instruments involved in the examples are described. The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

The abbreviations used in the present disclosure are explained as follows:
XRPD: X-ray Powder Diffraction
DSC: Differential Scanning calorimetry
TGA: Thermo Gravimetric Analysis
$^1$H NMR: Proton Nuclear Magnetic Resonance
HPLC: High Performance Liquid Chromatography
Instruments and methods used for data collection:
X-ray powder diffraction patterns in the present disclosure were acquired by a Bruker D2 PHASER X-ray powder diffractometer. The parameters of the X-ray powder diffraction method of the present disclosure are as follows:
X-ray Reflection: Cu, Kα
Kα1 (Å): 1.54060; Kα2 (Å): 1.54439
Kα2/Kα1 intensity ratio: 0.50
Voltage: 30 (kV)
Current: 10 (mA)
Scan range: from 3.0 degree to 40.0 degree
Differential scanning calorimetry (DSC) data in the present disclosure were acquired by a TA Q2000. The parameters of the DSC method of the present disclosure are as follows:
Heating rate: 10° C./min
Purge gas: nitrogen
Thermo gravimetric analysis (TGA) data in the present disclosure were acquired by a TA Q500. The parameters of the TGA method of the present disclosure are as follows:
Heating rate: 10° C./min
Purge gas: nitrogen Proton nuclear magnetic resonance spectrum data ($^1$H NMR) were collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/mL.

High Performance Liquid Chromatography (HPLC) data in the present disclosure were collected from an Agilent 1260, the parameters for purity test in the present disclosure are as follows:
1. Column: Ultimate LP-C18, 250×4.6 mm, 5 μm
2. Mobile Phase: A: 0.1% Phosphoric acid in H$_2$O (pH=3.5, TEA)
B: Acetonitrile
Gradient:

| Time (min) | % B |
|---|---|
| 0.0 | 20 |
| 9.0 | 34 |
| 11.0 | 40 |
| 18.0 | 50 |
| 22.0 | 70 |
| 30.0 | 70 |
| 31.0 | 20 |
| 40.0 | 20 |

3. 1.0 mL/min
4. Injection Volume: 10 μL
5. Detection wavelength: 230 nm
6. Column Temperature: 40° C.
7. Diluent: Acetonitrile According to the present disclosure, acalabrutinib and/or its salt used as a raw material is solid (crystalline and amorphous), semisolid, wax or oil. Preferably, compound I and/or its salt used as a raw material is a solid powder.

Acalabrutinib free base solid used in the following examples were prepared by known methods in the prior art, for example, the method disclosed in WO2017002095A1.

EXAMPLES

Figure 1:
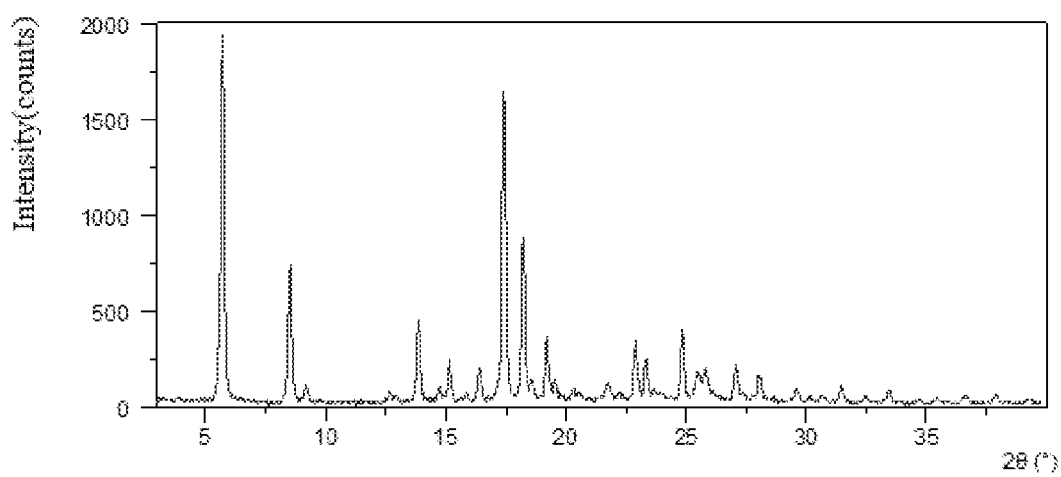
FIG. 1 shows an XRPD pattern of ethyl L-lactate solvate Form A in Example 1
Figure 2:
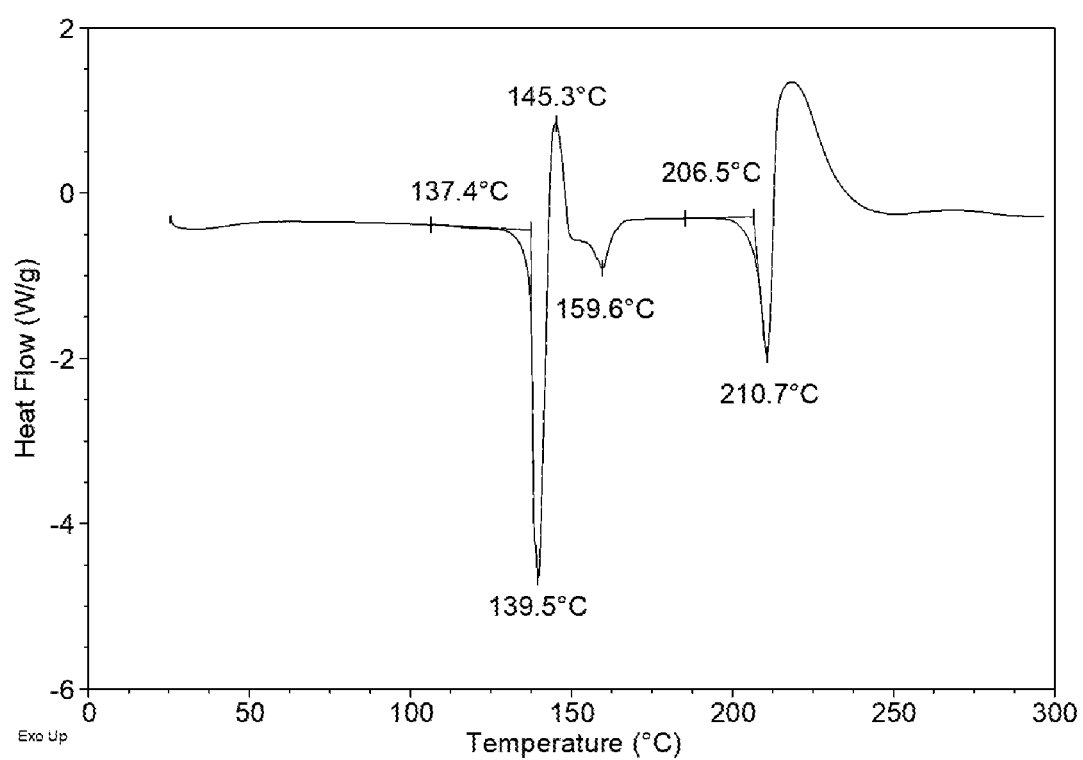
FIG. 2 shows a DSC curve of ethyl L-lactate solvate Form A in Example 1
Figure 3:
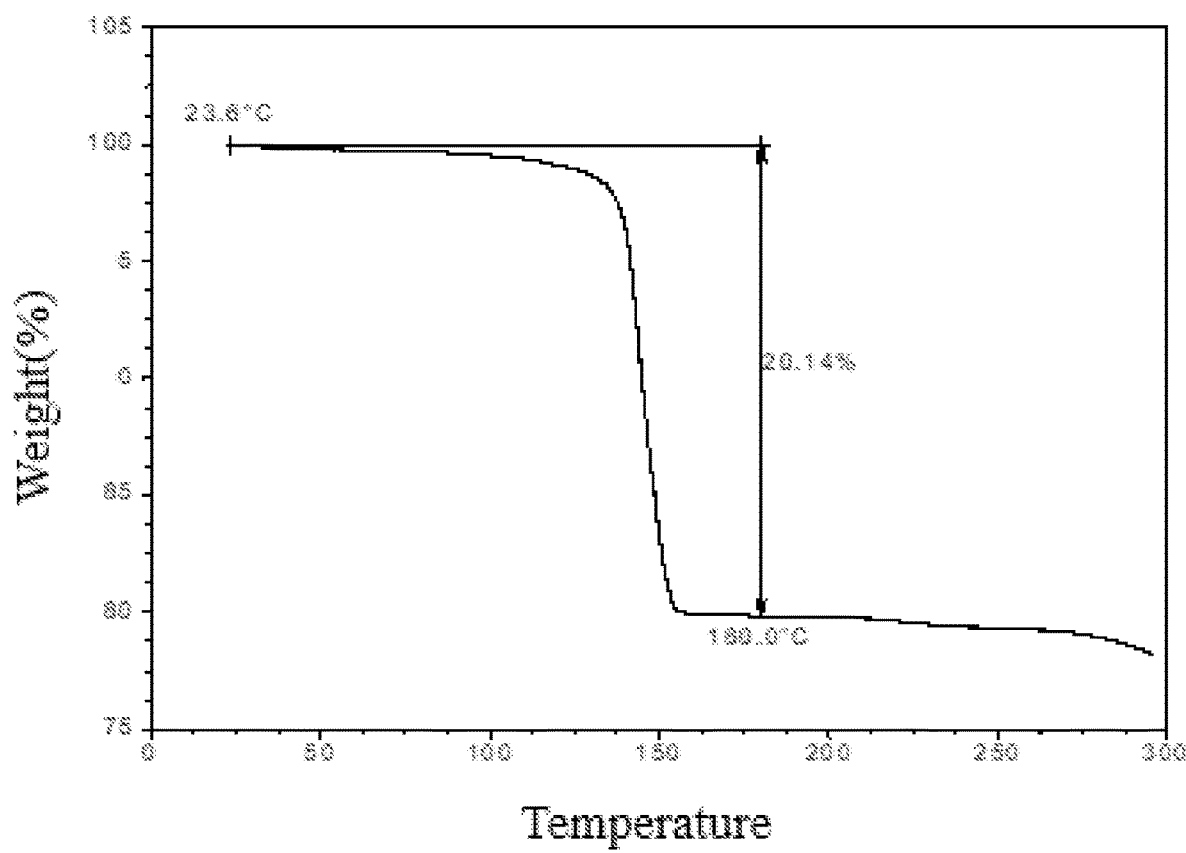
FIG. 3 shows a TGA curve of ethyl L-lactate solvate Form A in Example 1
Figure 4:
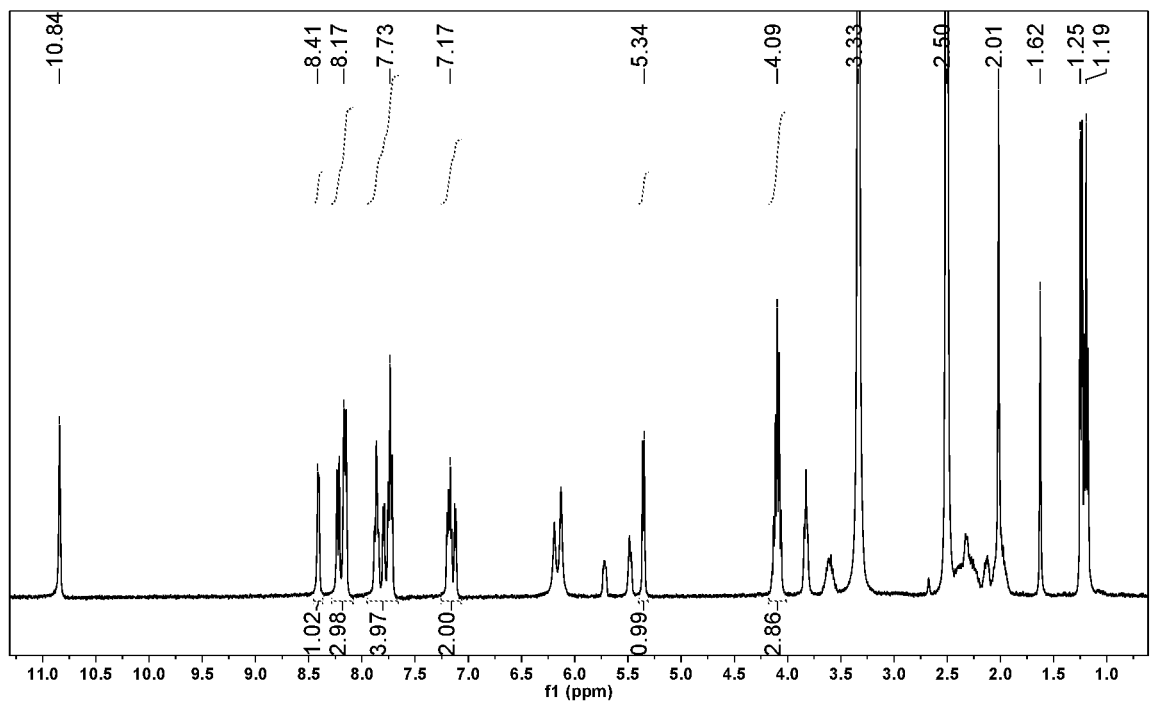
FIG. 4 shows a $^1$H NMR spectrum of ethyl L-lactate solvate Form A in Example 1

Example 1 Preparation of Ethyl L-Lactate Solvate Form A 2.50 g of acalabrutinib free base was weighed into a 100-mL crystallizer and 25 mL of ethyl L-lactate was added. The mixture was heated to 40° C., stirred for 8 hours, cooled to 20° C. and stirred overnight. Solids were obtained by isolation. The solid obtained in the present example was confirmed to be ethyl L-lactate solvate Form A. The XRPD pattern is substantially as depicted in FIG. 1, and the XRPD data are listed in Table 1. The DSC curve is substantially as depicted in FIG. 2. The first endothermic peak at around 137° C. corresponds to the desolvating endothermic peak. The TGA curve shows about 20.1% weight loss when heated to 180° C., which is substantially as depicted in FIG. 3. The $^1$H NMR spectrum is depicted in FIG. 4. According to the $^1$H NMR data, one mole of ethyl L-lactate solvate Form A contains about one mole of ethyl L-lactate. Ethyl L-lactate has characteristic chemical shift peaks at 1.25, 4.09 and 5.34.

TABLE 1

| 2θ (±0.2°) | d spacing | Intensity % |
|---|---|---|
| 5.72 | 15.45 | 100.00 |
| 8.54 | 10.35 | 36.36 |

TABLE 1-continued

| 2θ (±0.2°) | d spacing | Intensity % |
|---|---|---|
| 9.21 | 9.61 | 4.24 |
| 12.65 | 7.00 | 2.71 |
| 13.87 | 6.38 | 22.32 |
| 15.15 | 5.85 | 10.46 |
| 16.41 | 5.40 | 9.25 |
| 17.41 | 5.09 | 84.03 |
| 18.22 | 4.87 | 43.58 |
| 19.21 | 4.62 | 18.18 |
| 20.31 | 4.37 | 3.50 |
| 21.75 | 4.09 | 5.09 |
| 22.85 | 3.89 | 14.98 |
| 23.28 | 3.82 | 10.30 |
| 24.84 | 3.58 | 19.78 |
| 25.49 | 3.49 | 7.95 |
| 25.80 | 3.45 | 8.84 |
| 27.07 | 3.29 | 10.26 |
| 28.00 | 3.19 | 5.56 |
| 29.57 | 3.02 | 3.87 |
| 31.45 | 2.84 | 4.18 |
| 33.44 | 2.68 | 3.58 |
| 36.60 | 2.46 | 1.85 |
| 37.88 | 2.38 | 2.15 |

Example 2 Preparation of Ethyl L-Lactate Solvate Form A 1.23 g of acalabrutinib freebase was weighed into a 20-mL glass vial, and 12.0 mL of ethyl L-lactate/EtOAc (1:1, v/v) was added. The mixture was stirred magnetically at 50° C. for 3 days, 1.34 g of solid was obtained by isolation and drying. The obtained solid was confirmed to be Form A of the present disclosure. The XRPD data are listed in Table 2. Form A of the present example and Form A of Example 1 have identical or similar XRPD patterns, revealing that they are the same crystalline form and possess the same properties.

TABLE 2

| 2θ (±0.2°) | d spacing | Intensity % |
|---|---|---|
| 5.80 | 15.24 | 33.97 |
| 8.60 | 10.28 | 100.00 |
| 9.26 | 9.55 | 8.61 |
| 12.70 | 6.97 | 13.05 |
| 12.99 | 6.81 | 7.37 |
| 13.93 | 6.36 | 14.40 |
| 14.83 | 5.97 | 12.42 |
| 15.21 | 5.83 | 38.34 |
| 15.88 | 5.58 | 2.65 |
| 16.46 | 5.39 | 20.39 |
| 17.48 | 5.07 | 22.13 |
| 18.30 | 4.85 | 18.80 |
| 18.60 | 4.77 | 6.79 |
| 19.27 | 4.61 | 6.63 |
| 19.59 | 4.53 | 13.09 |
| 19.84 | 4.47 | 4.33 |
| 20.48 | 4.34 | 2.04 |
| 21.75 | 4.09 | 9.65 |
| 22.26 | 3.99 | 4.25 |
| 22.95 | 3.87 | 15.71 |
| 23.68 | 3.76 | 12.02 |
| 24.88 | 3.58 | 34.38 |
| 25.60 | 3.48 | 17.42 |
| 25.87 | 3.44 | 10.69 |
| 27.11 | 3.29 | 5.42 |
| 28.07 | 3.18 | 8.91 |

Example 3 Purification Effect of Ethyl L-Lactate Solvate Form A

HPLC was applied to test the chemical purity of freebase and ethyl L-lactate solvate Form A of the present disclosure, and the purity change was calculated.

HPLC purity test results show that ethyl L-lactate solvate Form A of the present disclosure has substantial purification effect. The purity of freebase is 98.93%, while ethyl L-lactate solvate Form A of the present disclosure has a purity of 99.63% and the purity is increased by 0.70%.

Example 4 Stability of Ethyl L-Lactate Solvate Form A

Figure 25:
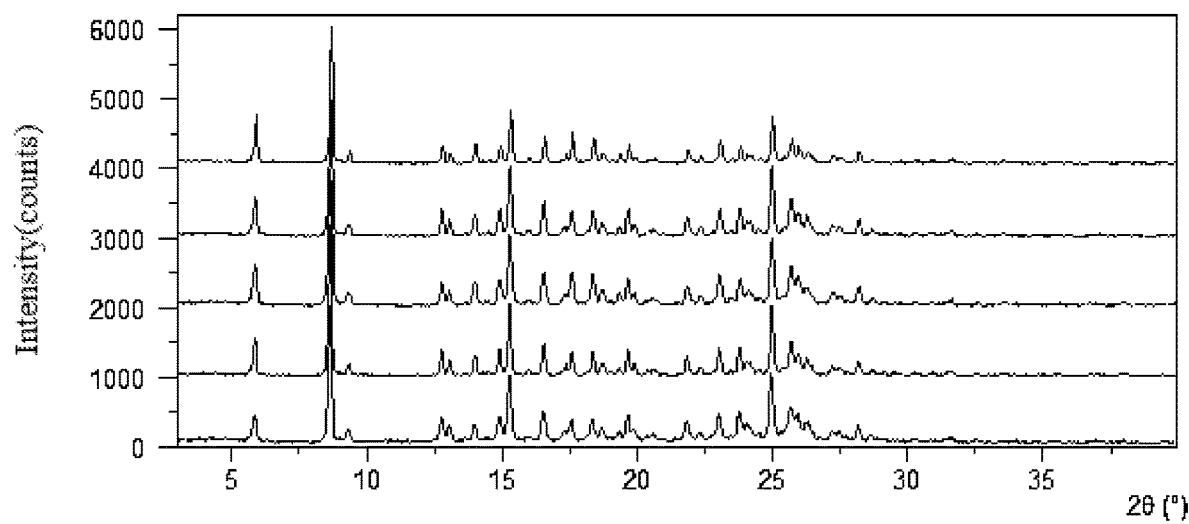
FIG. 25 shows an XRPD pattern overlay of Form A from stability study (from top to bottom: initial, stored at 25° C./60% RH for 2 months in closed dish, stored at 25° C./60% RH for 2 months in open dish, stored at 40° C./75% RH for 2 months in closed dish, stored at 40° C./75% RH for 2 months in open dish)

Approximately 10 mg of Form A of the present disclosure was weighed and stored at different conditions of 25° C./60% RH in open dish, 25° C./60% RH in closed dish, 40° C./75% RH in open dish, and 40° C./75% RH in closed dish. Crystalline forms were checked by XRPD. The results are shown in Table 3, and the XRPD overlay is shown in FIG. 25.

TABLE 3

| Initial solid form | Condition | Storage time | Solid form |
|---|---|---|---|
| Form A | Initial | — | Form A |
|  | 25° C./60% RH in closed dish | 2 months | Form A |
|  | 25° C./60% RH in open dish | 2 months | Form A |
|  | 40° C./75% RH in closed dish | 2 months | Form A |
|  | 40° C./75% RH in open dish | 2 months | Form A |

The results show that Form A kept stable for at least 2 months at 25° C./60% RH in open dish, 25° C./60% RH in closed dish, 40° C./75% RH in open dish, and 40° C./75% RH in closed dish. It shows that Form A has good stability under both long-term and accelerated conditions.

Example 5 Intrinsic Dissolution Rate of Ethyl L-Lactate Solvate Form A

Figure 26:
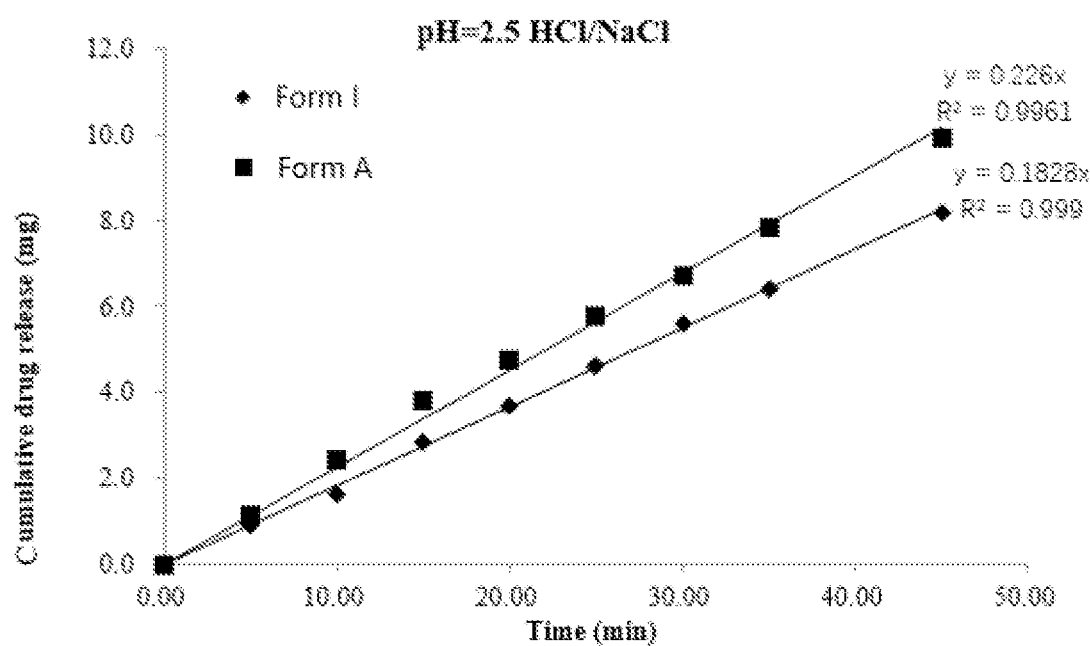
FIG. 26 shows the intrinsic dissolution profile of Form A

Approximately 200 mg of Form A and Form I in WO2017002095A1 were added into the die, compressed at 10 kN and held for 1 minute to obtain a pellet having a surface area of 0.5 cm$^2$. The whole tool with the pellet was transferred to a dissolution apparatus to test the intrinsic dissolution rate. Test conditions are shown in Table 4. Dissolution profile is presented in FIG. 26, and dissolution data are presented in Table 5. The slope (mg/min) was calculated according to the data within 0-45 minutes. Intrinsic dissolution rate (IDR, mg/min/cm$^2$) was further calculated according to the slope. IDR results are presented in Table 6.

TABLE 4

| | |
|---|---|
| Instrument | Agilent 708DS |
| Medium | pH = 2.5 HCl/NaCl aqueous solution |
| Volume | 500 mL |
| Speed | 100 rpm |
| Temperature | 37° C. |
| Sampling Time | 5, 10, 15, 20, 25, 30, 35, 45 min |
| Supplement medium | No (Sampling 1.0 mL at each time point) |

TABLE 5

| | Cumulative dissolution (mg) | |
|---|---|---|
| Time (min) | Form I | Form A |
| 0 | 0.00 | 0.00 |
| 5 | 0.92 | 1.13 |
| 10 | 1.64 | 2.42 |
| 15 | 2.81 | 3.80 |
| 20 | 3.66 | 4.73 |
| 25 | 4.62 | 5.79 |
| 30 | 5.58 | 6.72 |
| 35 | 6.40 | 7.83 |
| 45 | 8.16 | 9.93 |

TABLE 6

| Solid form | IDR (mg/min/cm$^2$) |
|---|---|
| Form I in WO2017002095A1 | 0.3656 |
| Form A | 0.4520 |

The results show that the IDR of Form A is 1.2 times higher than that of Form I in WO2017002095A1.

Example 6 Hygroscopicity of Ethyl L-Lactate Solvate Form A

Figure 27:
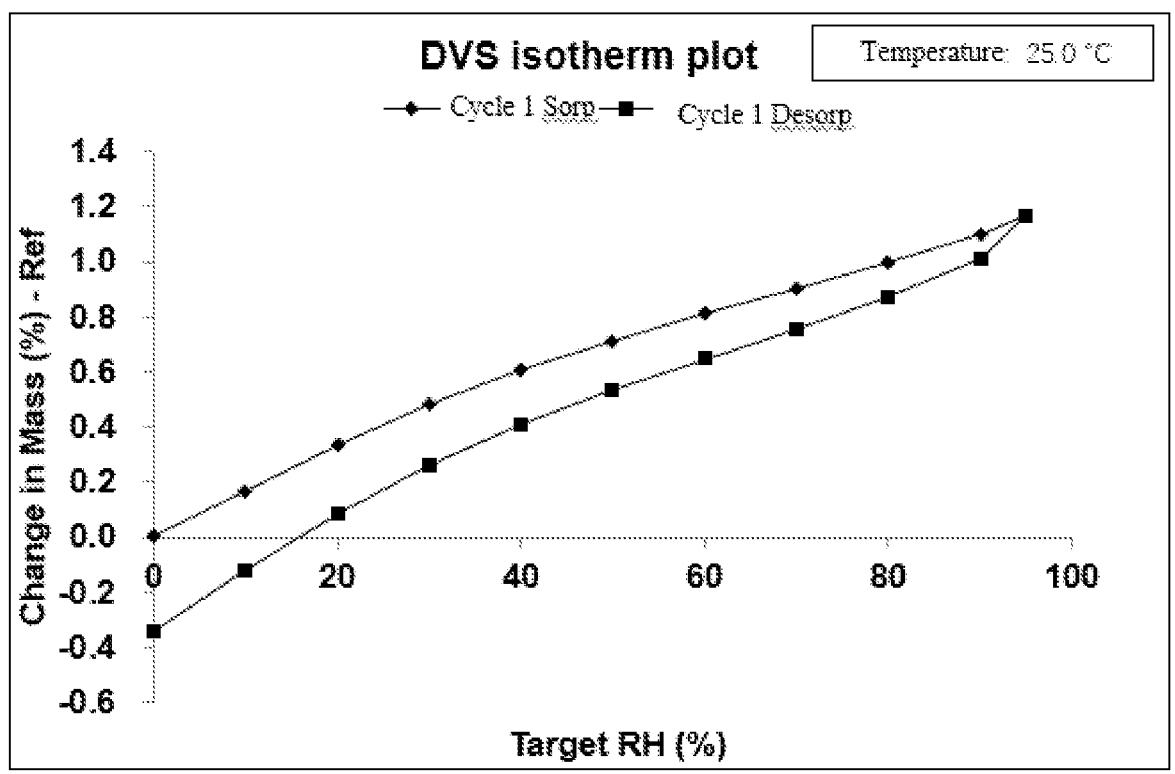
FIG. 27 shows a DVS plot of Form A
Figure 28:
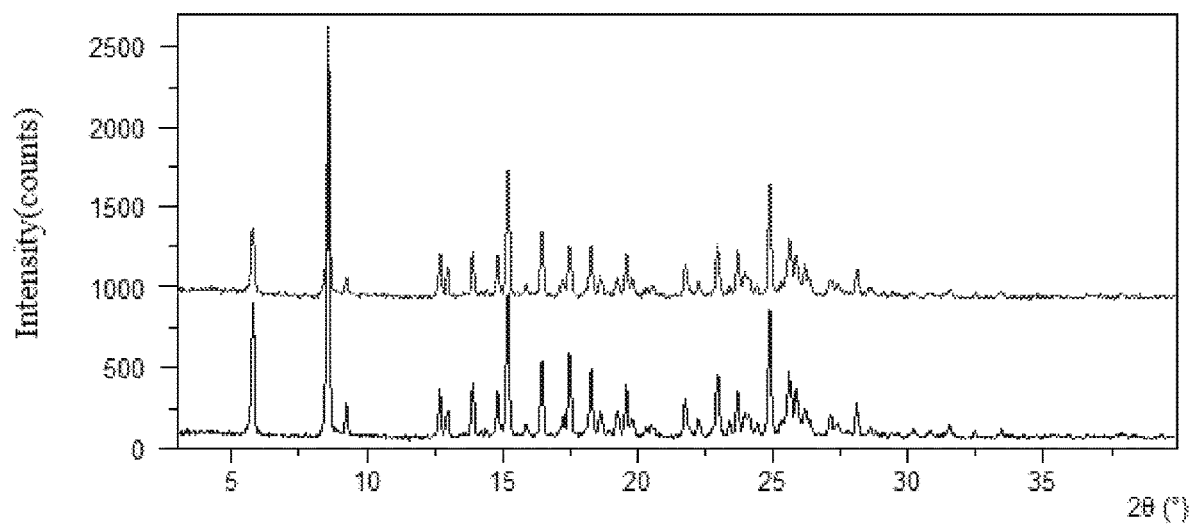
FIG. 28 shows an XRPD pattern overlay of Form A before and after DVS test (bottom: before DVS; top: after DVS)

Dynamic vapor sorption (DVS) was applied to test hygroscopicity of Form A with about 10 mg of sample. Weight changes at each relative humidity were recorded in a cycle of 0-95%-0 RH at 25° C.±1° C. DVS plot is substantially as depicted in FIG. 27, and XRPD pattern overlay before and after DVS is shown in FIG. 28.

Description and definition of hygroscopicity (general notice 9103 drug hygroscopicity test guidelines in 2015 edition of Chinese Pharmacopoeia, test at 25° C.+/−1° C., 80% RH).

deliquescent: Sufficient water is absorbed to form a liquid;

very hygroscopic: Increase in mass is equal to or greater than 15 percent;

hygroscopic: Increase in mass is less than 15 percent and equal to or greater than 2 percent;

slightly hygroscopic: Increase in mass is less than 2 percent and equal to or greater than 0.2 percent.

non hygroscopic or almost non hygroscopic: Increase in mass is less than 0.2%.

The results show that Form A is slightly hygroscopic with a weight gain of 0.99% at 80% RH.

Example 7 Compressibility of Ethyl L-Lactate Solvate Form A

Approximately 80 mg of Form A and Form I in WO2017002095A1 were weighed into the dies of a φ6 mm round tooling, compressed at 10 kN manually, then stored in a desiccator for 24 hours until complete elastic recovery. Radial crushing force (hardness, H) was tested with an intelligent tablet hardness tester. Diameter (D) and thickness (L) were tested with a caliper. Tensile strength of the powder that with different hardness was calculated with the following formula: $T=2H/\pi DL$. Under a certain force, the greater the tensile strength, the better the compressibility. The results are presented in Table 7.

TABLE 7

| Solid Form | Tensile strength (MPa) |
|---|---|
| Form I in WO2017002095A1 | Unable to be compressed into tablet |
| Form A | 1.35 |

The results indicate that Form A has higher tensile strength and better compressibility compared with Form I in WO2017002095A1.

Example 8 Adhesiveness of Ethyl L-Lactate Solvate Form A

Approximately 30 mg of Form A and Form I in WO2017002095A1 were weighed, added into the dies of a φ8 mm round tooling, compressed at 10 kN and held for about 30 s. The amount of material sticking to the punch was weighed. The compression was repeated twice and the cumulative amount and average amount of material sticking to the punch during the compression were recorded. Detailed experimental results are shown in Table 8.

TABLE 8

| Solid form | Cumulative amount (μg) | Average amount (μg) |
|---|---|---|
| Form I in WO2017002095A1 | 90 | 45 |
| Form A | 80 | 40 |

Test results indicate that the amount sticking to the punch of Form I in WO2017002095A1 is higher than of that of Form A. The adhesiveness of Form A is superior to that of Form I in WO2017002095A1.

Example 9 Flowability of Ethyl L-Lactate Solvate Form A

Compressibility index or Carr index is usually utilized to evaluate the flowability of powder and granules during the drug product process. Compressibility index test method is as follows: a certain amount of powder was added into a measuring cylinder and bulk volume was recorded. Then the powder was tapped to make it in the tightest state and the tapped volume was recorded. The bulk density ($\rho_o$) and tapped density ($\rho_f$) were calculated. Compressibility index was calculated according to $c=(\rho_f-\rho_o)/\rho_f$.

Criteria of flowability is shown in Table 9.

TABLE 9

| Compressibility index (%) | Flowability |
|---|---|
| ≤10 | Excellent |
| 11-15 | Good |
| 16-20 | Fair |
| 21-25 | Passable |
| 26-31 | poor |
| 32-37 | Very poor |
| >38 | Very, very poor |

Flowability evaluation results of Form A are presented in Table 10, indicating that Form A has good flowability.

TABLE 10

| Solid form | Bulk density ($\rho_o$, g/mL) | Tapped density ($\rho_f$, g/mL) | Compressibility index (%) | Flowability |
|---|---|---|---|---|
| Form A | 0.269 | 0.303 | 11% | Good |

Figure 9:
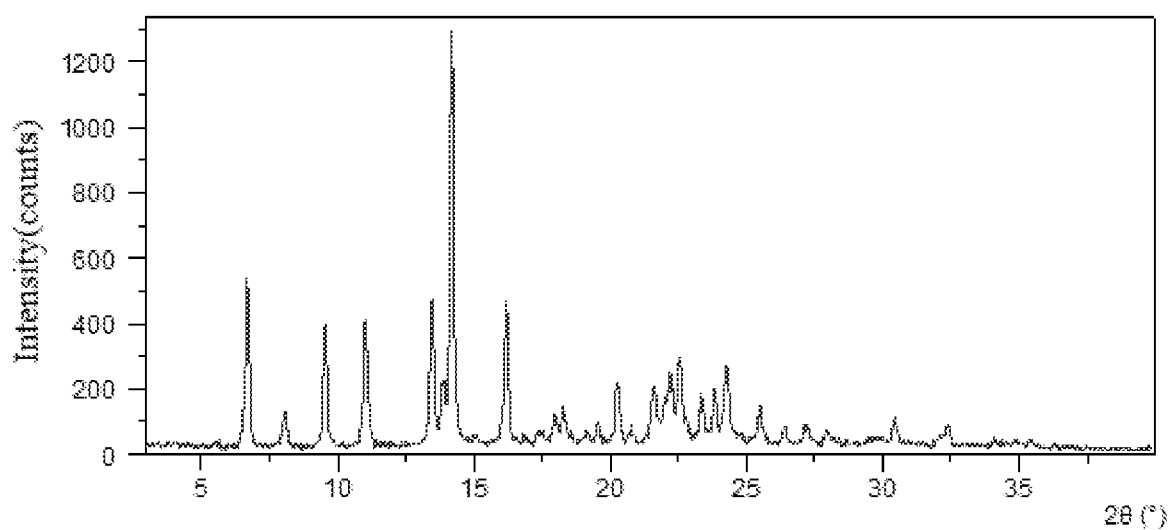
FIG. 9 shows an XRPD pattern of glycerol solvate Form D in Example 10
Figure 10:
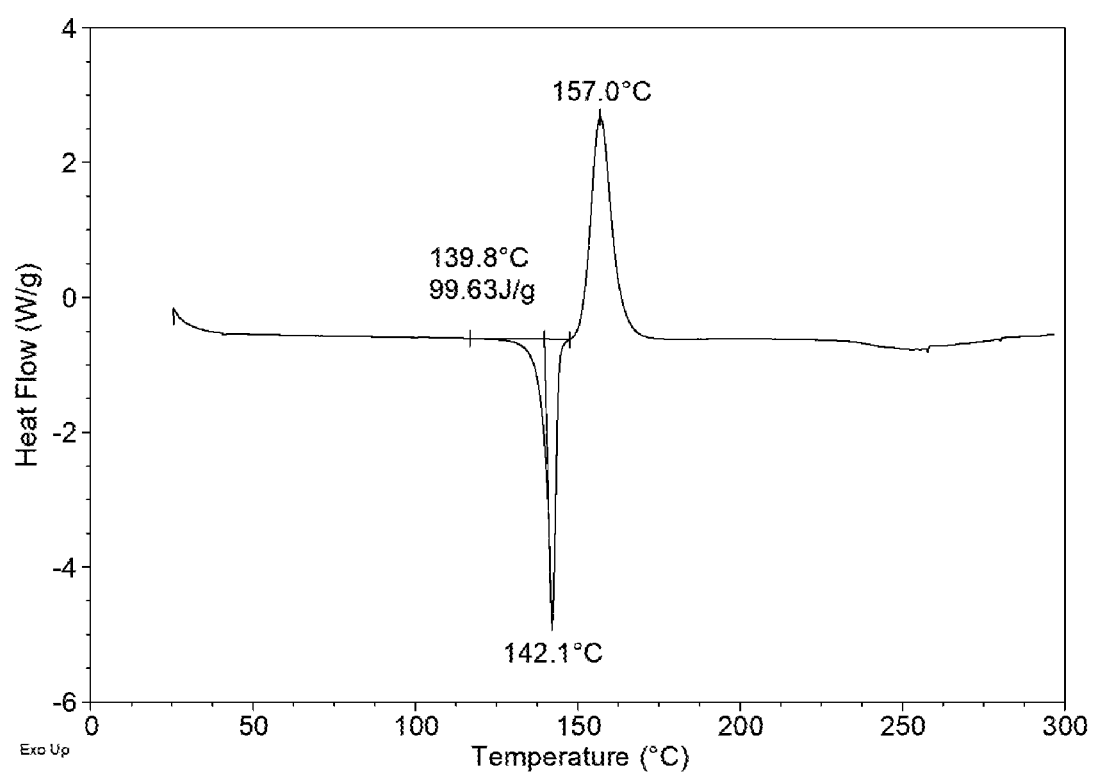
FIG. 10 shows a DSC curve of glycerol solvate Form D in Example 10
Figure 11:
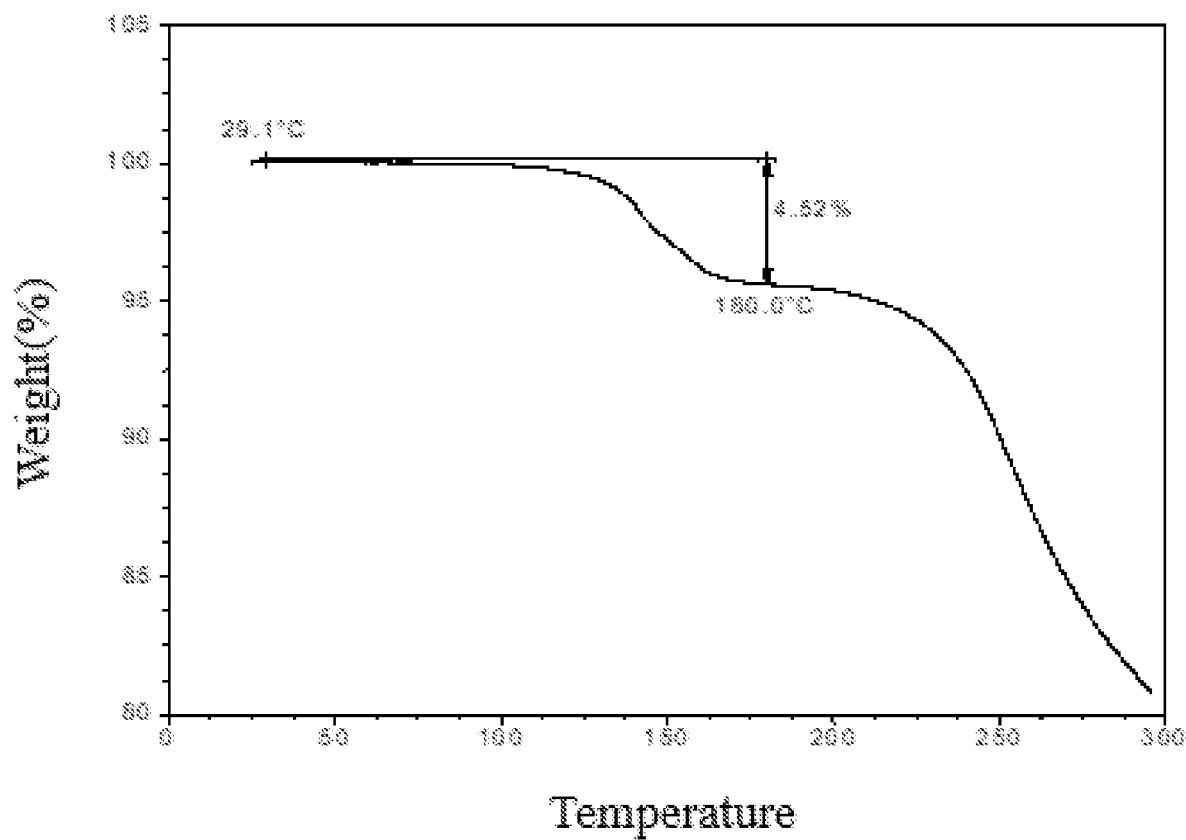
FIG. 11 shows a TGA curve of glycerol solvate Form D in Example 10
Figure 12:
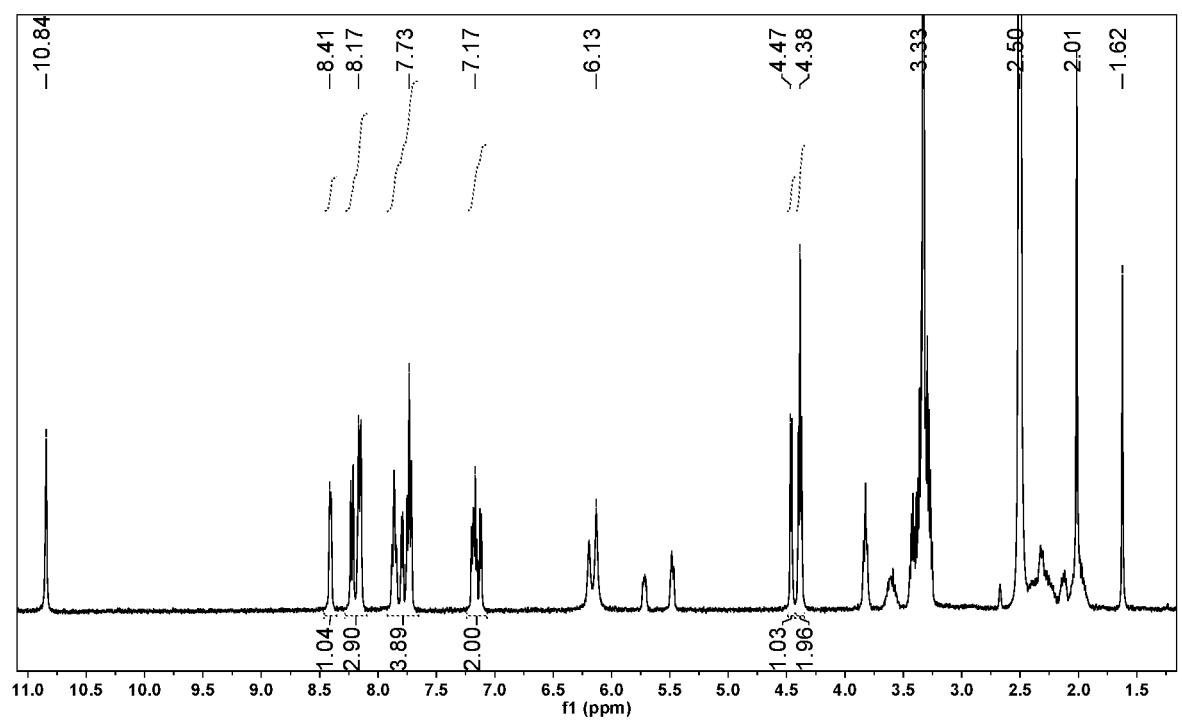
FIG. 12 shows a $^1$H NMR spectrum of glycerol solvate Form D in Example 10

Example 10 Preparation of Glycerol Solvate Form D 54.5 mg of acalabrutinib freebase was weighed into a 1.5-mL glass vial and 1.0 mL of glycerol was added. The mixture was stirred at 40° C. overnight, and 0.5 mL of glycerol was added. Then the mixture was heated to 60° C. and stirred overnight. Solids were obtained by isolation. The solid obtained in the present example was confirmed to be glycerol solvate Form D. The XRPD pattern is substantially as depicted in FIG. 9, and the XRPD data are listed in Table 11. The DSC curve is substantially as depicted in FIG. 10. The first endothermic peak at around 140° C. corresponds to the desolvating endothermic peak. The TGA curve shows about 4.5% weight loss when heated to 180° C., which is substantially as depicted in FIG. 11. The $^1$H NMR spectrum is depicted in FIG. 12. According to the $^1$H NMR data, one mole of glycerol solvate Form D contains about one mole of glycerol. Glycerol has characteristic chemical shift peaks at 4.38, 4.47 and peaks overlapped with water peak at 3.33.

TABLE 11

| 2θ (±0.2°) | d spacing | Intensity % |
|---|---|---|
| 6.68 | 13.24 | 39.74 |
| 8.06 | 10.97 | 8.29 |
| 9.55 | 9.26 | 29.75 |
| 11.02 | 8.03 | 30.67 |
| 13.45 | 6.58 | 35.87 |
| 13.86 | 6.39 | 15.29 |
| 14.21 | 6.23 | 100.00 |
| 16.21 | 5.47 | 34.96 |
| 17.99 | 4.93 | 4.14 |
| 19.57 | 4.54 | 5.20 |
| 20.26 | 4.38 | 14.82 |
| 21.59 | 4.12 | 13.56 |
| 22.55 | 3.94 | 20.88 |
| 23.84 | 3.73 | 13.45 |
| 24.27 | 3.67 | 18.38 |
| 25.51 | 3.49 | 9.21 |
| 26.40 | 3.38 | 4.04 |
| 27.20 | 3.28 | 4.38 |
| 30.44 | 2.94 | 6.12 |
| 32.38 | 2.76 | 4.53 |

Example 11 Preparation of Glycerol Solvate Form D 1.24 g of acalabrutinib freebase was weighed into a 20-mL glass vial, and 12.0 mL of glycerol/IPA (1:2, v/v) was added. The mixture was stirred magnetically at 50° C. for 3 days, 1.36 g of solid was obtained by isolation and drying. The obtained solid was confirmed to be Form D of the present disclosure. The XRPD data are listed in Table 12. Form D of the present example and Form D of example 10 have identical or similar XRPD patterns, revealing that they are the same crystalline form and possess the same properties.

TABLE 12

| 2θ (±0.2°) | d spacing | Intensity % |
| --- | --- | --- |
| 6.72 | 13.14 | 37.17 |
| 8.08 | 10.95 | 9.94 |
| 9.56 | 9.25 | 38.32 |
| 11.05 | 8.01 | 32.54 |
| 13.47 | 6.57 | 35.23 |
| 13.90 | 6.37 | 19.03 |
| 14.20 | 6.24 | 100.00 |
| 16.23 | 5.46 | 39.04 |
| 17.98 | 4.93 | 10.07 |
| 18.28 | 4.85 | 10.79 |
| 20.30 | 4.38 | 16.00 |
| 20.80 | 4.27 | 3.29 |
| 21.65 | 4.11 | 15.81 |
| 22.23 | 4.00 | 18.02 |
| 22.53 | 3.95 | 23.09 |
| 23.37 | 3.81 | 10.49 |
| 23.85 | 3.73 | 11.57 |
| 24.31 | 3.66 | 18.14 |
| 25.54 | 3.49 | 10.45 |
| 26.43 | 3.37 | 3.44 |
| 27.21 | 3.28 | 6.41 |
| 30.46 | 2.94 | 8.37 |
| 32.43 | 2.76 | 5.96 |

Example 12 Purity of Glycerol Solvate Form D

HPLC was applied to test the chemical purity of freebase and glycerol solvate Form D of the present disclosure, and the purity change was calculated.

HPLC purity test results show that glycerol solvate Form D of the present disclosure has substantial purification effect. The purity of freebase is 98.93%, while glycerol solvate Form D of the present disclosure has a purity of 99.49% and the purity is increased by 0.56%.

Example 13 Stability of Glycerol Solvate Form D

Figure 29:
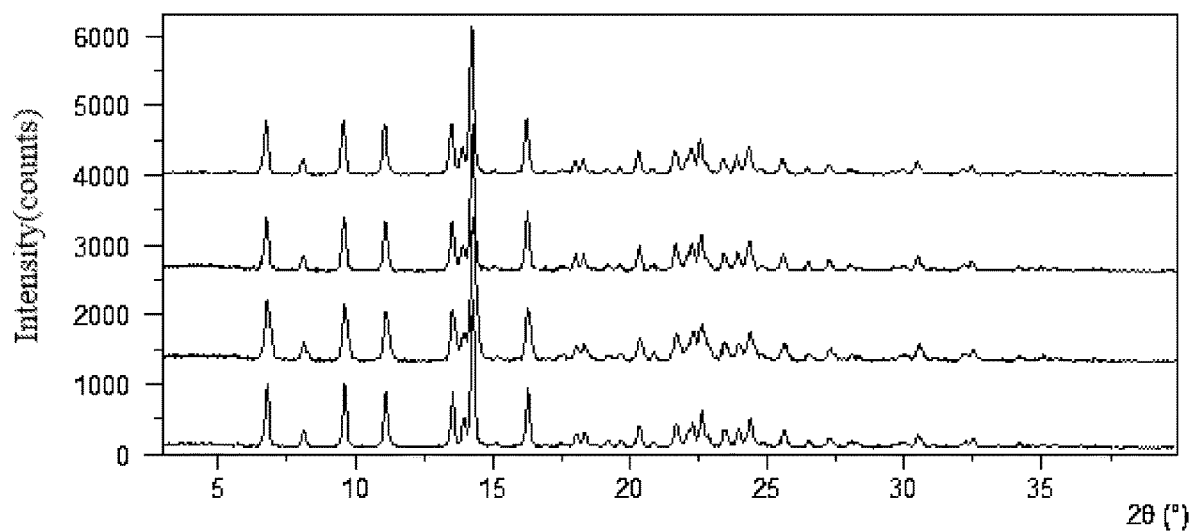
FIG. 29 shows an XRPD pattern overlay of Form D from stability study (from top to bottom: initial, stored at 25° C./60% RH for 2 months in closed dish, stored at 25° C./60% RH for 2 months in open dish, stored at 40° C./75% RH for 2 months in closed dish)

Approximately 10 mg of Form D of the present disclosure was weighed and stored at different conditions of 25° C./60% RH in closed dish, 25° C./60% RH in open dish, 40° C./75% RH in closed dish. Crystalline form was checked by XRPD. The results are shown in Table 13, and the XRPD overlay is shown in FIG. 29.

TABLE 13

| Initial solid form | Condition | Storage time | Solid form |
| --- | --- | --- | --- |
| Form D | 25° C./60% RH in closed dish | 2 months | Form D |
| | 25° C./60% RH in open dish | 2 months | Form D |
| | 40° C./75% RH in closed dish | 2 months | Form D |

The results show that Form D kept stable for at least 2 months at 25° C./60% RH in closed dish, 25° C./60% RH in open dish, and 40° C./75% RH in closed dish, indicating Form D possesses good stability.

Example 14 Intrinsic Dissolution Rate of Glycerol Solvate Form D

Figure 40:
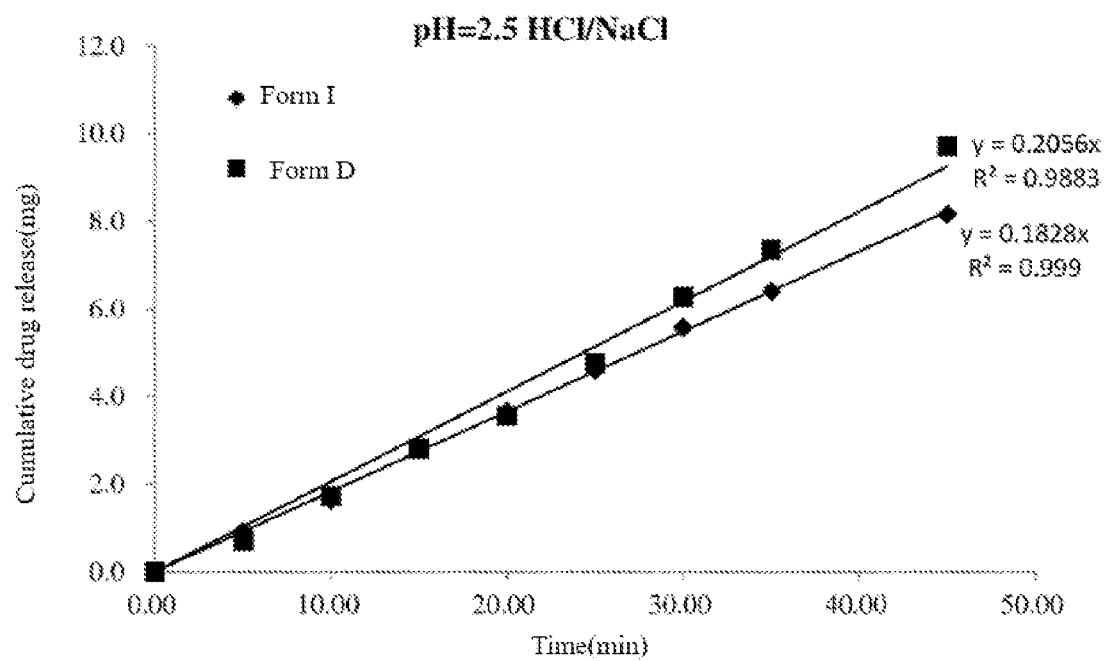
FIG. 40 shows the intrinsic dissolution profile of Form D

Approximately 200 mg of Form D and Form I in WO2017002095A1 were added into the die, compressed at 10 kN and held for 1 minute to obtain a pellet having a surface area of 0.5 cm$^2$. The whole tool with the pellet was transferred to a dissolution apparatus to test the intrinsic dissolution rate. Test conditions are shown in Table 14. Dissolution profile is presented in FIG. 40 and dissolution data are presented in Table 15. The slope (mg/min) was calculated according to the data within 0-45 minutes. Intrinsic dissolution rate (IDR, mg/min/cm$^2$) was further calculated according to the slope. IDR results are presented in Table 16.

TABLE 14

| | |
| --- | --- |
| Instrument | Agilent 708DS |
| Medium | pH = 2.5 HCl/NaCl aqueous solution |
| Volume | 500 mL |
| Speed | 100 rpm |
| Temperature | 37° C. |
| Sampling Time | 5, 10, 15, 20, 25, 30, 35, 45 min |
| Supplement medium | No (Sampling 1.0 mL at each time point) |

TABLE 15

| Time (min) | Cumulative dissolution (mg) | |
| --- | --- | --- |
| | Form I | Form D |
| 0 | 0.00 | 0.00 |
| 5 | 0.92 | 0.70 |
| 10 | 1.64 | 1.73 |
| 15 | 2.81 | 2.82 |
| 20 | 3.66 | 3.57 |
| 25 | 4.62 | 4.77 |
| 30 | 5.58 | 6.26 |
| 35 | 6.40 | 7.36 |
| 45 | 8.16 | 9.72 |

TABLE 16

| Solid form | IDR (mg/min/cm$^2$) |
| --- | --- |
| Form I in WO2017002095A1 | 0.3656 |
| Form D | 0.4112 |

The results show that the IDR of Form D is 1.1 times higher than that of Form I in WO2017002095A1.

Example 15 Compressibility of Glycerol Solvate Form D

Approximately 80 mg of Form D and Form I in WO2017002095A1 were weighed into the dies of a φ6 mm round tooling, compressed at 10 kN manually, and then stored in a desiccator for 24 hours until complete elastic recovery. Radial crushing force (hardness, H) was tested with an intelligent tablet hardness tester. Diameter (D) and thickness (L) were tested with a caliper. Tensile strength of the powder with different hardness was calculated with the following formula: T=2H/πDL. Under a certain force, the greater the tensile strength, the better the compressibility. The results are presented in Table 17.

TABLE 17

| Solid form | Tensile strength (MPa) |
| --- | --- |
| Form I in WO2017002095A1 | Unable to be compressed into a tablet |
| Form D | 0.83 |

The results indicate that Form D has higher tensile strength and better compressibility compared with Form I in WO2017002095A1.

Figure 13:
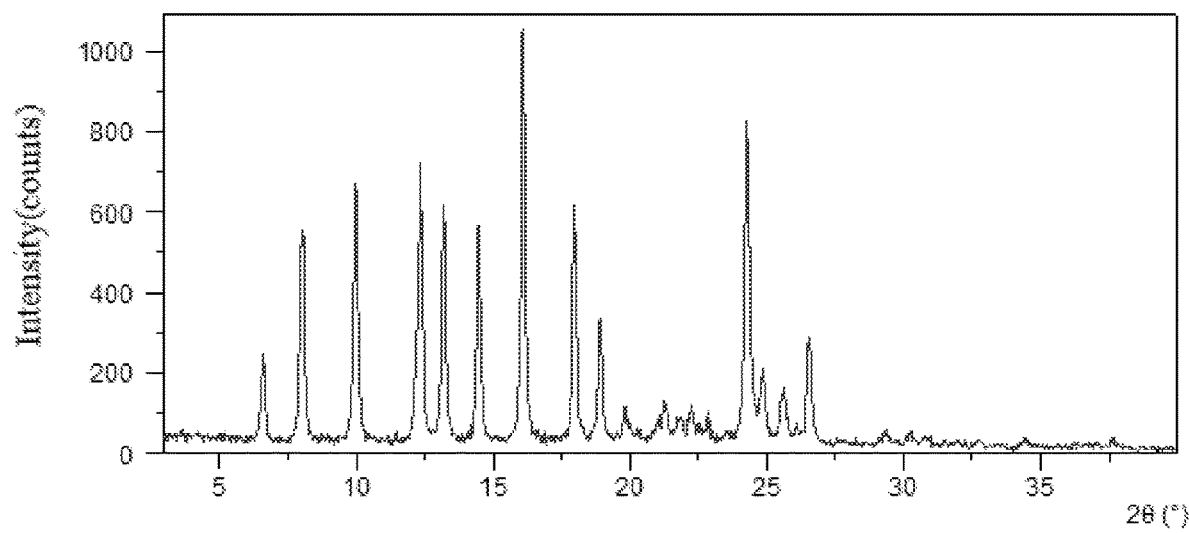
FIG. 13 shows an XRPD pattern of (S)-1,2-propanediol solvate Form F in Example 16
Figure 14:
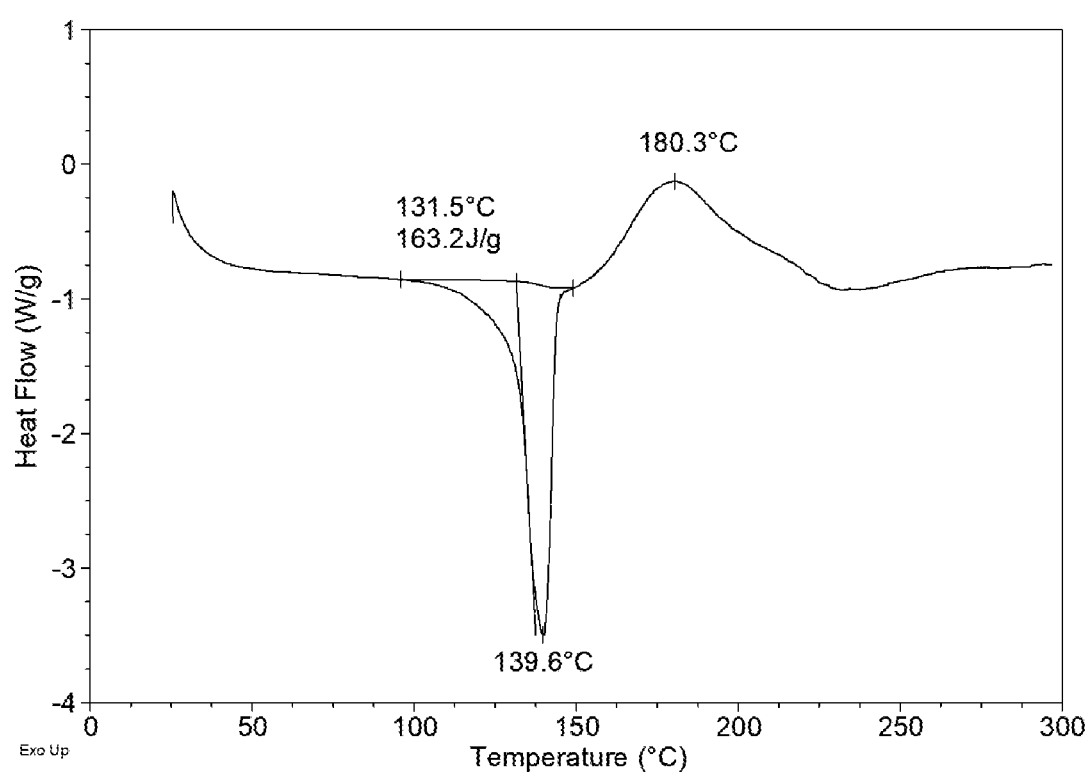
FIG. 14 shows a DSC curve of (S)-1,2-propanediol solvate Form F in Example 16
Figure 15:
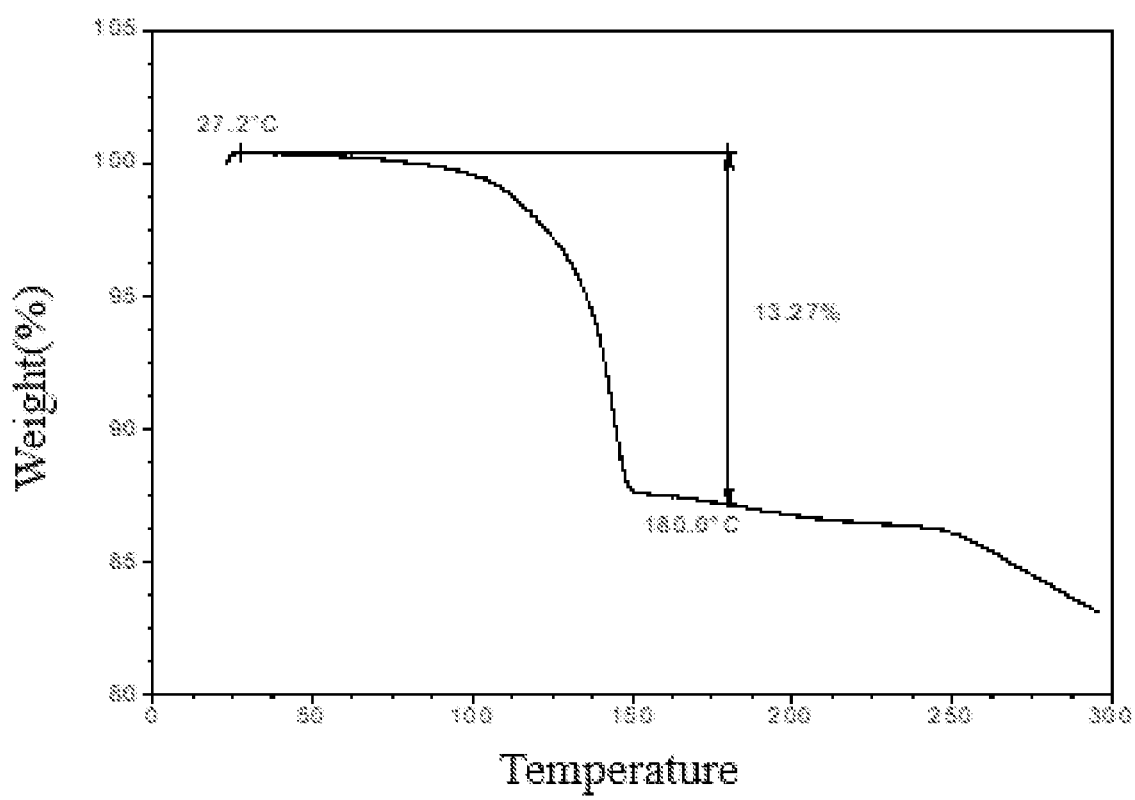
FIG. 15 shows a TGA curve of (S)-1,2-propanediol solvate Form F in Example 16
Figure 16:
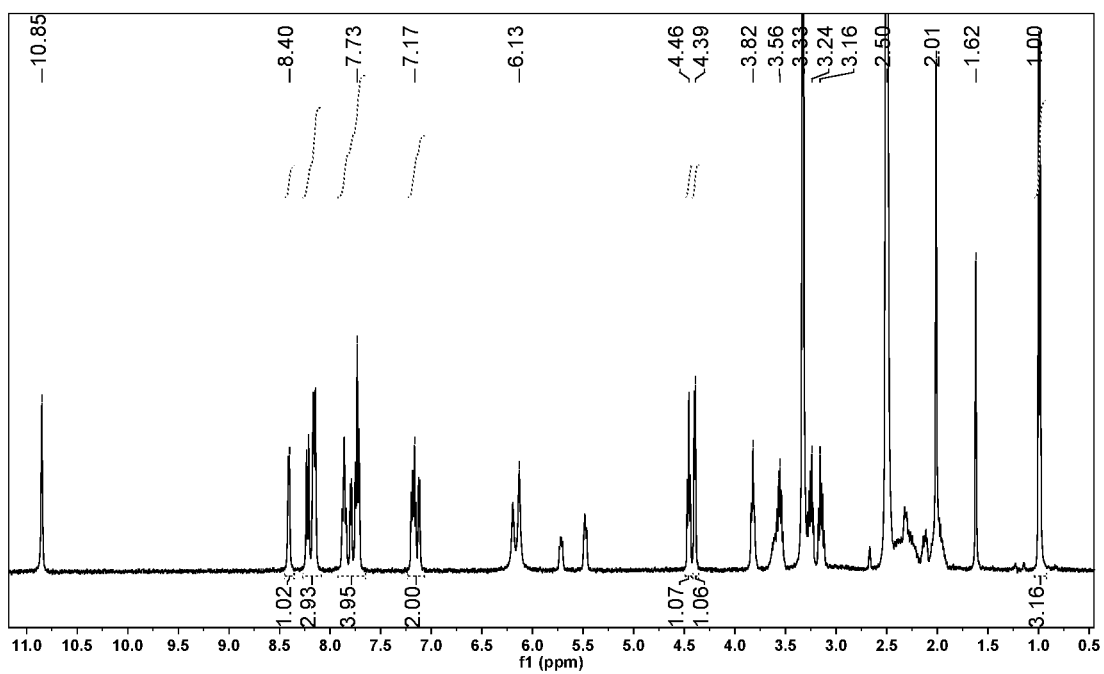
FIG. 16 shows a $^1$H NMR spectrum of (S)-1,2-propanediol solvate Form F in Example 16

Example 16 Preparation of (S)-1,2-propanediol Solvate Form F 53.1 mg of acalabrutinib freebase was weighed into a 1.5-mL glass vial and 0.5 mL of (S)-1,2-propanediol was added. The mixture was stirred at room temperature overnight. Solids were obtained by isolation. The solid obtained in the present example was confirmed to be (S)-1,2-propanediol solvate Form F. The XRPD pattern is substantially as depicted in FIG. 13, and the XRPD data are listed in Table 18. The DSC curve is substantially as depicted in FIG. 14. The first endotherm peak at around 131° C. corresponds to the desolvating endothermic peak. The TGA curve shows about 13.3% weight loss when heated to 180° C., which is substantially as depicted in FIG. 15. The $^1$H NMR spectrum is depicted in FIG. 16. According to the $^1$H NMR data, one mole of (S)-1,2-propanediol solvate Form F contains about one mole of (S)-1,2-propanediol. (S)-1,2-propanediol has characteristic chemical shift peaks at around 1.00, 3.16, 3.24, 3.56, 4.39 and 4.46.

TABLE 18

| 2θ (±0.2°) | d spacing | Intensity % |
|---|---|---|
| 6.62 | 13.36 | 19.97 |
| 8.08 | 10.95 | 47.34 |
| 10.00 | 8.85 | 62.32 |
| 12.39 | 7.14 | 67.91 |
| 13.24 | 6.69 | 57.05 |
| 14.47 | 6.12 | 45.63 |
| 16.10 | 5.51 | 100.00 |
| 18.00 | 4.93 | 57.06 |
| 18.94 | 4.69 | 29.72 |
| 19.91 | 4.46 | 6.05 |
| 21.31 | 4.17 | 9.67 |
| 22.28 | 3.99 | 8.47 |
| 24.29 | 3.66 | 78.07 |
| 24.87 | 3.58 | 16.87 |
| 25.61 | 3.48 | 11.82 |
| 26.59 | 3.35 | 25.52 |

Example 17 Preparation of (S)-1,2-propanediol Solvate Form F 1.22 g of solid was weighed into a 20-mL glass vial and 12.0 mL of (S)-1,2-propanediol/EtOAc (1:1, v/v) was added. The mixture was stirred magnetically at 50° C. for three days, 1.22 g of solid was obtained by isolation and drying. The obtained solid was confirmed to be Form F of the present disclosure. The XRPD data are listed in Table 19. Form F of the present example and Form F of example 16 have identical or similar XRPD patterns, revealing that they are the same crystalline form and possess the same properties.

TABLE 19

| 2θ (±0.2°) | d spacing | Intensity % |
|---|---|---|
| 6.55 | 13.50 | 15.76 |
| 7.98 | 11.07 | 45.42 |
| 9.93 | 8.91 | 62.59 |
| 12.31 | 7.19 | 72.52 |
| 13.14 | 6.74 | 57.65 |
| 14.41 | 6.15 | 46.02 |
| 16.04 | 5.52 | 95.59 |
| 17.91 | 4.95 | 49.20 |
| 18.86 | 4.71 | 34.52 |
| 19.77 | 4.49 | 6.61 |
| 21.24 | 4.18 | 9.33 |

TABLE 19-continued

| 2θ (±0.2°) | d spacing | Intensity % |
|---|---|---|
| 21.70 | 4.10 | 7.35 |
| 22.17 | 4.01 | 8.77 |
| 22.81 | 3.90 | 10.18 |
| 24.19 | 3.68 | 100.00 |
| 24.79 | 3.59 | 19.82 |
| 25.58 | 3.48 | 17.00 |
| 26.48 | 3.37 | 33.37 |
| 29.34 | 3.04 | 6.28 |

Example 18 Purity of (S)-1,2-propanediol Solvate Form F

HPLC was applied to test the chemical purity of freebase and (S)-1,2-propanediol solvate Form F of the present disclosure, and the purity change was calculated.

HPLC purity test results show that (S)-1,2-propanediol solvate Form F of the present disclosure has substantial purification effect. The purity of freebase is 98.93%, while (S)-1,2-propanediol solvate Form F of the present disclosure has a purity of 99.80% and the purity is increased by 0.87%.

Example 19 Stability of (S)-1,2-propanediol Solvate Form F

Figure 30:
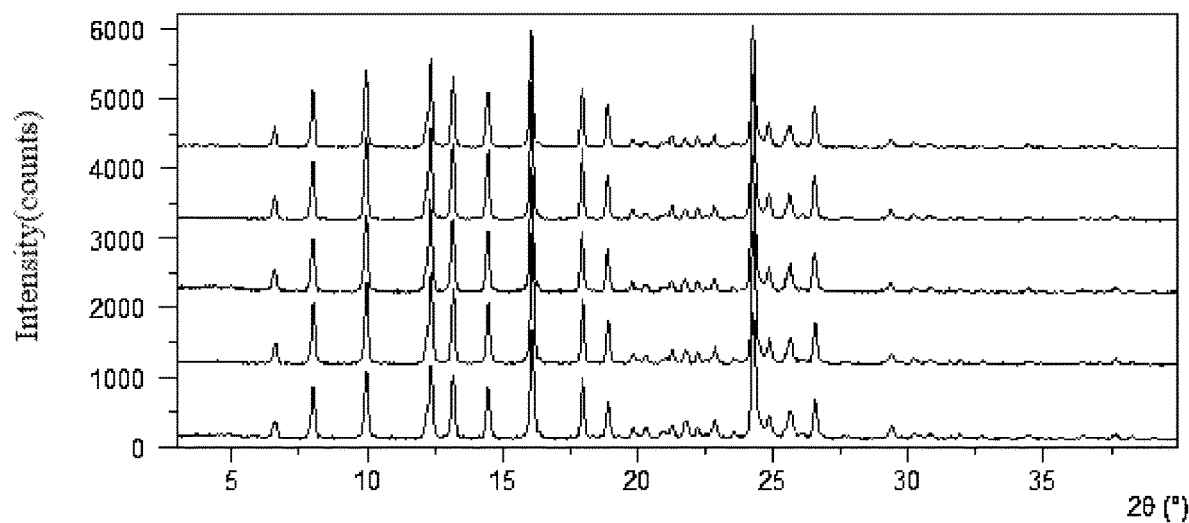
FIG. 30 shows an XRPD pattern overlay of Form F from stability study (from top to bottom: initial, stored at 25° C./60% RH for 2 months in closed dish, stored at 25° C./60% RH for 2 months in open dish, being stored at 40° C./75% RH for 2 months in closed dish, stored at 40° C./75% RH for 2 months in open dish)

Approximately 10 mg of Form F of the present disclosure was weighed and stored at different conditions of 25° C./60% RH in closed dish, 25° C./60% RH in open dish, and 40° C./75% RH in closed dish, 40° C./75% RH in open dish. Crystalline forms were checked by XRPD. The results are shown in Table 20, and the XRPD overlay is shown in FIG. 30.

TABLE 20

| Initial solid form | Condition | Storage time | Solid form |
|---|---|---|---|
| Form F | 25° C./60% RH in closed dish | 2 months | Form F |
|  | 25° C./60% RH in open dish | 2 months | Form F |
|  | 40° C./75% RH in closed dish | 2 months | Form F |
|  | 40° C./75% RH in open dish | 2 months | Form F |

The results show that Form F kept stable for at least 2 months at 25° C./60% RH in closed dish, 25° C./60% RH in open dish, 40° C./75% RH in closed dish, and 40° C./75% RH in open dish. It shows that Form F has good stability under both long-term and accelerated conditions.

Example 20 Intrinsic Dissolution Rate of (S)-1,2-propanediol Solvate Form F

Figure 31:
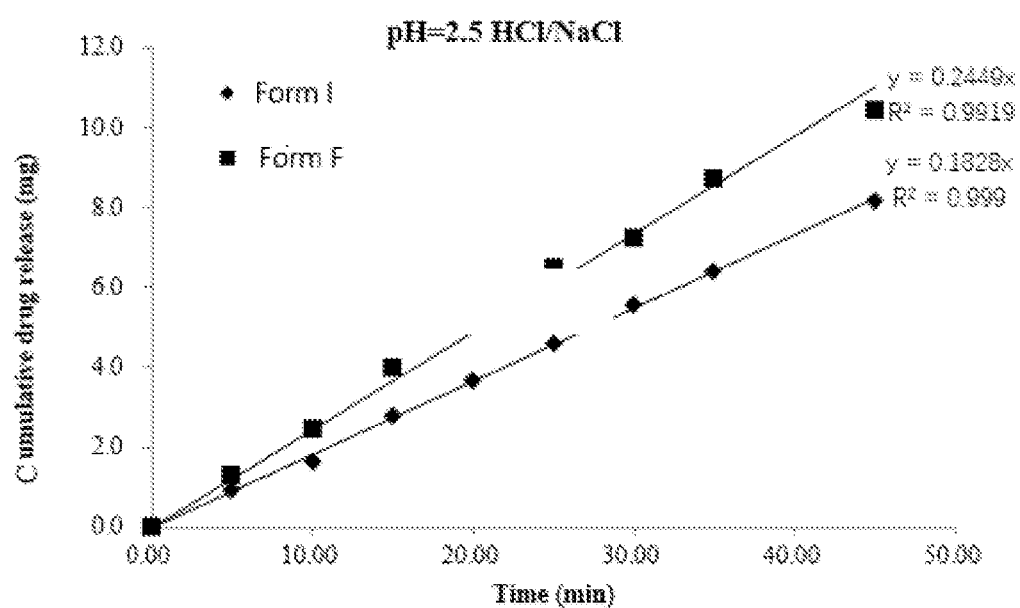
FIG. 31 shows the intrinsic dissolution profile of Form F

Approximately 200 mg of Form F and Form I in WO2017002095A1 were added into the die, compressed at 10 kN and held for 1 minute to obtain a pellet having a surface area of 0.5 cm$^2$. The whole tool with the pellet was transferred to a dissolution apparatus to test the intrinsic dissolution. Test conditions are shown in Table 21. Dissolution profile is presented in FIG. 31 and dissolution data are presented in Table 22. The slope (mg/min) was calculated according to the data within 0-45 minutes. Intrinsic dissolution rate (IDR, mg/min/cm$^2$) was further calculated according to the slope. IDR results are presented in Table 23.

TABLE 21

| Instrument | Agilent 708DS |
| --- | --- |
| Medium | pH = 2.5 HCl/NaCl aqueous solution |
| Volume | 500 mL |
| Speed | 100 rpm |
| Temperature | 37° C. |
| Sampling Time | 5, 10, 15, 20, 25, 30, 35, 45 min |
| Supplement medium | No (Sampling 1.0 mL at each time point) |

TABLE 22

| Time | Cumulative dissolution (mg) | |
| --- | --- | --- |
| (min) | Form I | Form F |
| 0 | 0.00 | 0.00 |
| 5 | 0.92 | 1.31 |
| 10 | 1.64 | 2.47 |
| 15 | 2.81 | 3.99 |
| 20 | 3.66 | 5.30 |
| 25 | 4.62 | 6.50 |
| 30 | 5.58 | 7.26 |
| 35 | 6.40 | 8.74 |
| 45 | 8.16 | 10.44 |

TABLE 23

| Solid form | IDR (mg/min/cm$^2$) |
| --- | --- |
| Form I in WO2017002095A1 | 0.3656 |
| Form F | 0.4898 |

The results show that the IDR of Form F is 1.3 times higher than that of Form I in WO2017002095A1.

Example 21 Hygroscopicity of (S)-1,2-propanediol Solvate Form F

Figure 32:
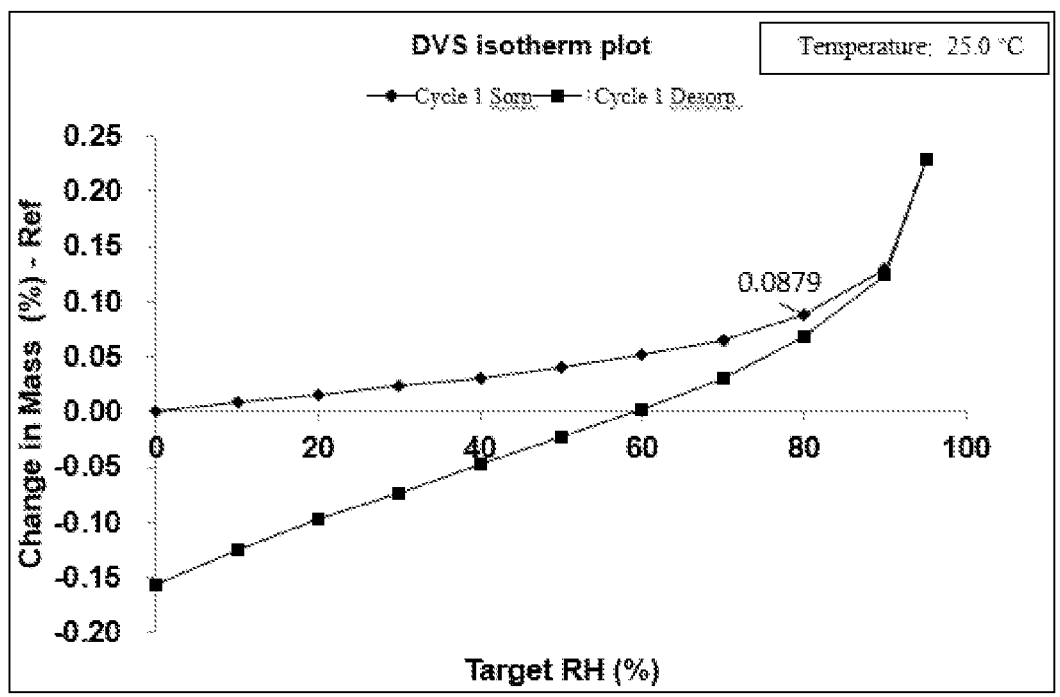
FIG. 32 shows a DVS plot of Form F
Figure 33:
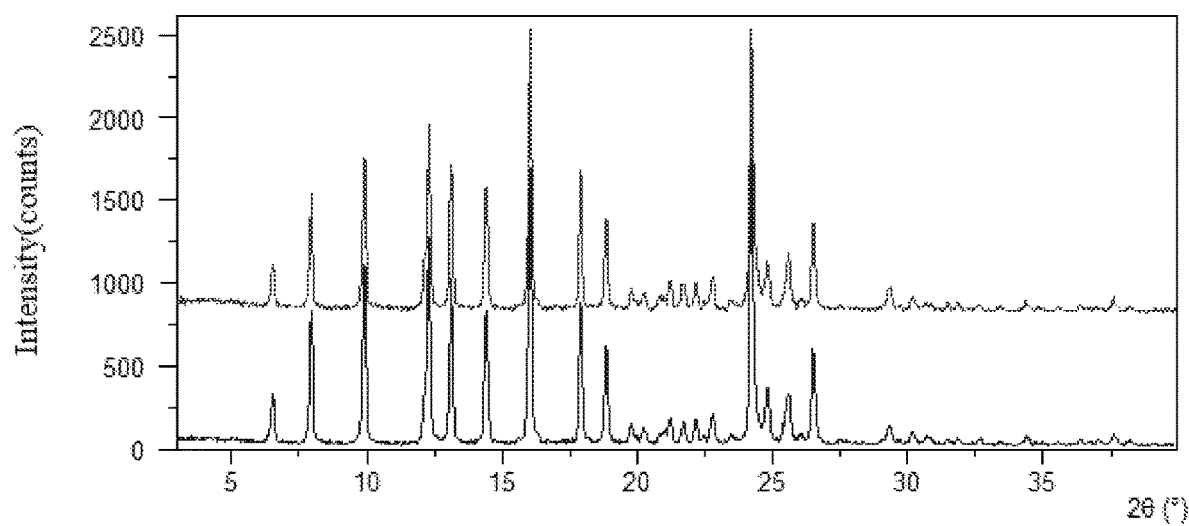
FIG. 33 shows an XRPD pattern overlay of Form F before and after DVS test (bottom: before DVS; top: after DVS)

Dynamic vapor sorption (DVS) was applied to test hygroscopicity of Form F with about 10 mg of sample. Weight changes at each relative humidity were recorded in a cycle of 0-95%-0 RH at 25° C.±1° C. DVS plot is substantially as depicted in FIG. 32, and XRPD patterns before and after DVS are compared in FIG. 33.

Description and definition of hygroscopicity (general notice 9103 drug hygroscopicity test guidelines in 2015 edition of Chinese Pharmacopoeia, test at 25° C. +/−1° C., 80% RH).

deliquescent: Sufficient water is absorbed to form a liquid;
very hygroscopic: Increase in mass is equal to or greater than 15 percent;
hygroscopic: Increase in mass is less than 15 percent and equal to or greater than 2 percent;
slightly hygroscopic: Increase in mass is less than 2 percent and equal to or greater than 0.2 percent.
non hygroscopic or almost non hygroscopic: Increase in mass is less than 0.2%.

The results show that Form F is non hygroscopic or almost non hygroscopic with a weight gain of 0.09% at 80% RH.

Example 22 Compressibility of (S)-1,2-propanediol Solvate Form F

Approximately 80 mg of Form F and Form I in WO2017002095A1 were weighed into the dies of a φ6 mm round tooling, compressed at 10 kN manually, and then stored in a desiccator for 24 hours until complete elastic recovery. Radial crushing force (hardness, H) was tested with an intelligent tablet hardness tester. Diameter (D) and thickness (L) were tested with caliper. Tensile strength of the powder with different hardness was calculated with the following formula: $T=2H/\pi DL$. Under a certain force, the greater the tensile strength, the better the compressibility. The results are presented in Table 24.

TABLE 24

| Solid Form | Tensile strength (MPa) |
| --- | --- |
| Form I in WO2017002095A1 | Unable to be compressed into a tablet |
| Form F | 1.02 |

The results indicate that Form F has higher tensile strength and better compressibility compared with Form I in WO2017002095A1.

Example 23 Adhesiveness of (S)-1,2-propanediol Solvate Form F

Approximately 30 mg of Form F and Form I in WO2017002095A1 were weighed, added into the dies of a φ8 mm round tooling, compressed at 10 kN and held for about 30 s. The amount of material sticking to the punch was weighed. The compression was repeated twice and the cumulative amount and average amount of material sticking to the punch during the compression were recorded. Detailed experimental results are summarized in Table 25.

TABLE 25

| Solid form | Cumulative amount (μg) | Average amount (μg) |
| --- | --- | --- |
| Form I in WO2017002095A1 | 90 | 45 |
| Form F | 60 | 30 |

Test results indicate that the amount sticking to the punch of Form I in WO2017002095A1 is higher than of that of Form F. The adhesiveness of Form F is superior to that of Form I in WO2017002095A1.

Example 24 Flowability of (S)-1,2-propanediol Solvate Form F

Compressibility index or Carr index is usually utilized to evaluate the flowability of powder and granules during the drug product process. Compressibility index test method is as follows: a certain amount of powder was added into a measuring cylinder and bulk volume was recorded. Then the powder was tapped to make it in the tightest state and the tapped volume was recorded. The bulk density ($\rho_0$), tapped density ($\rho_f$) were calculated and compressibility index was calculated according to c=(pf-po)/pf.

Criteria of flowability is shown in Table 26.

TABLE 26

| Compressibility index (%) | Flowability |
| --- | --- |
| ≤10 | Excellent |
| 11-15 | Good |

TABLE 26-continued

| Compressibility index (%) | Flowability |
| --- | --- |
| 16-20 | Fair |
| 21-25 | Passable |
| 26-31 | poor |
| 32-37 | Very poor |
| >38 | Very, very poor |

Flowability evaluation results of Form F are presented in Table 27, indicating that Form F has good flowability.

TABLE 27

| Solid form | Bulk density ($\rho_0$, g/mL) | Tapped density ($\rho_f$, g/mL) | Compressibility index (%) | Flowability |
| --- | --- | --- | --- | --- |
| Form F | 0.185 | 0.216 | 14% | Good |

Figure 17:
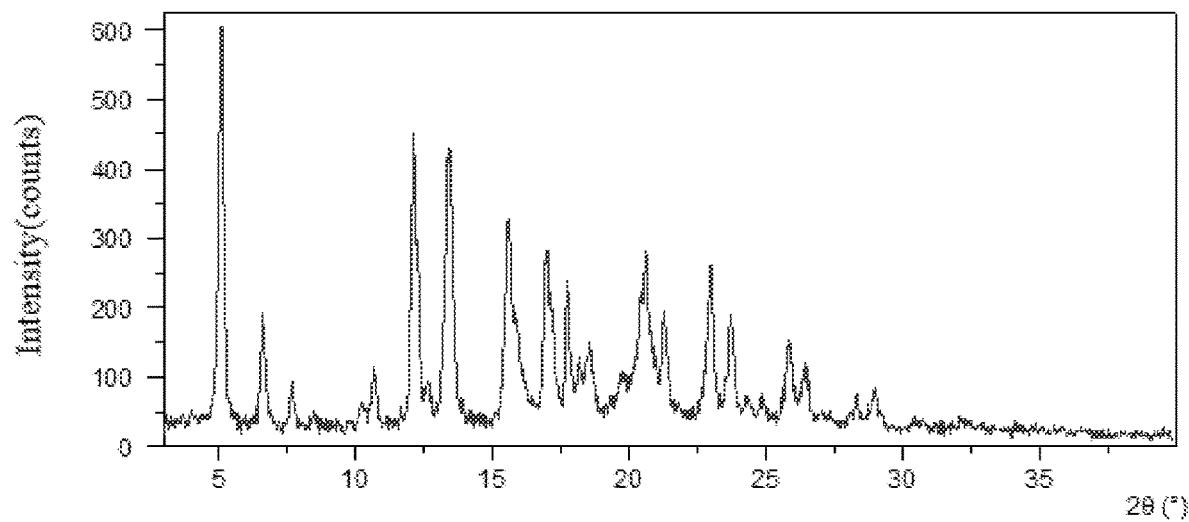
FIG. 17 shows an XRPD pattern of (R)-1,2-propanediol solvate Form G in Example 25
Figure 18:
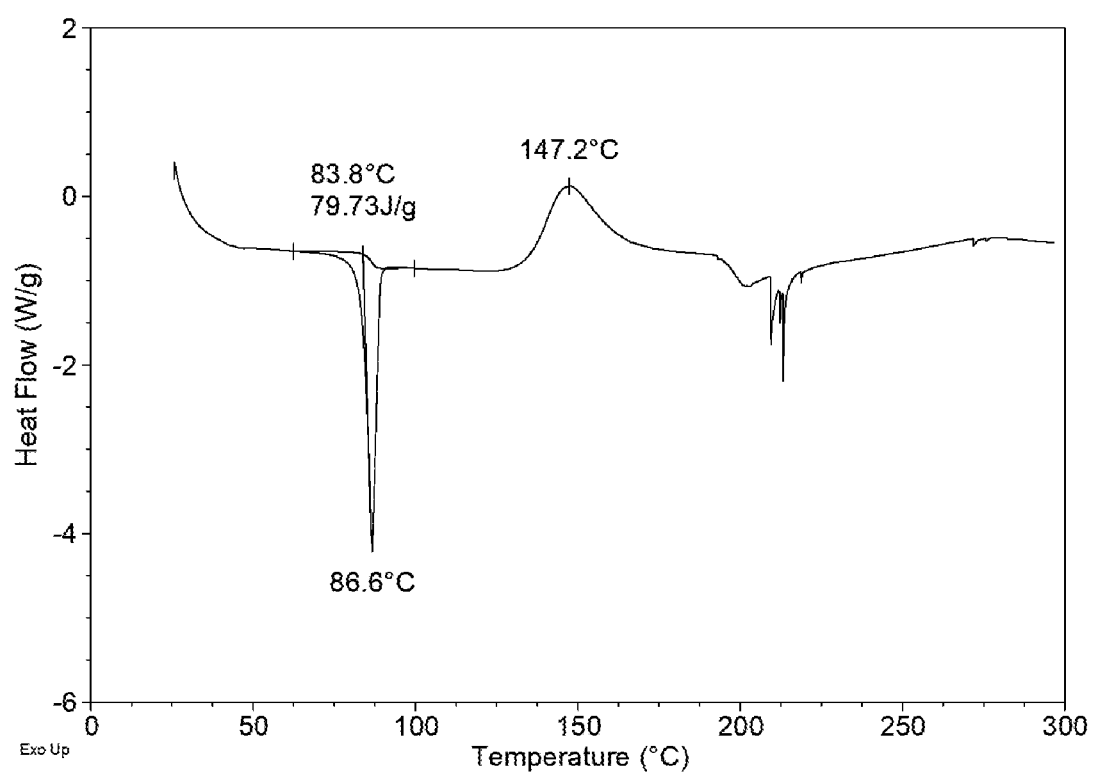
FIG. 18 shows a DSC curve of (R)-1,2-propanediol solvate Form G in Example 25
Figure 19:
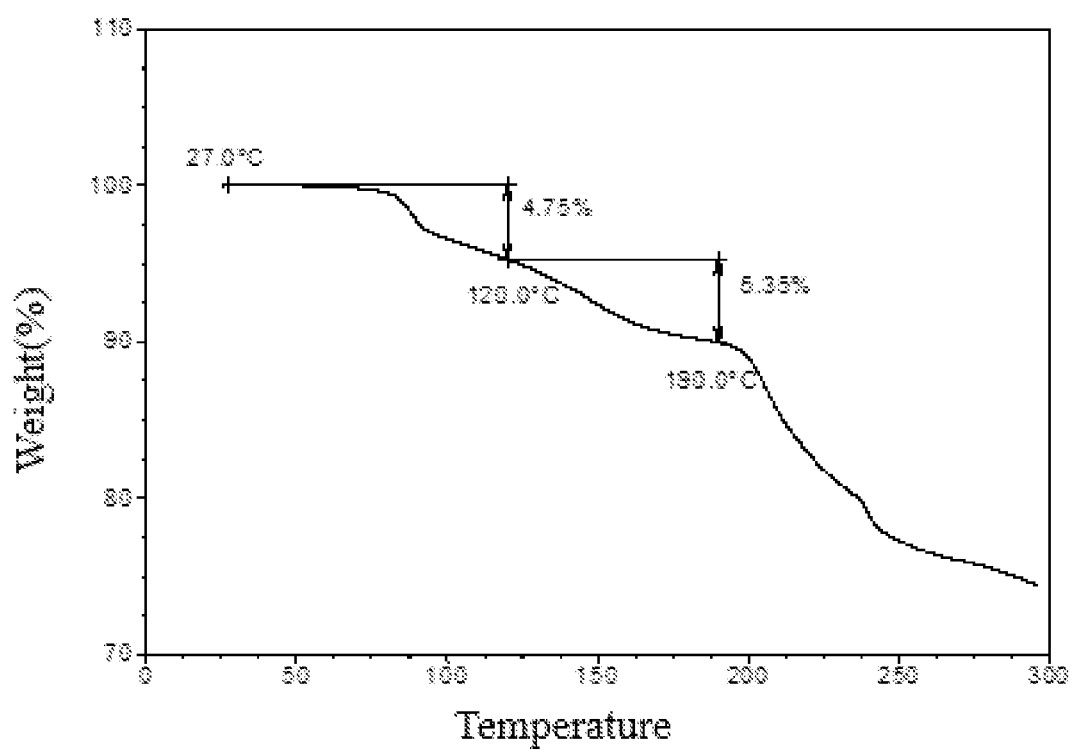
FIG. 19 shows a TGA curve of (R)-1,2-propanediol solvate Form G in Example 25
Figure 20:
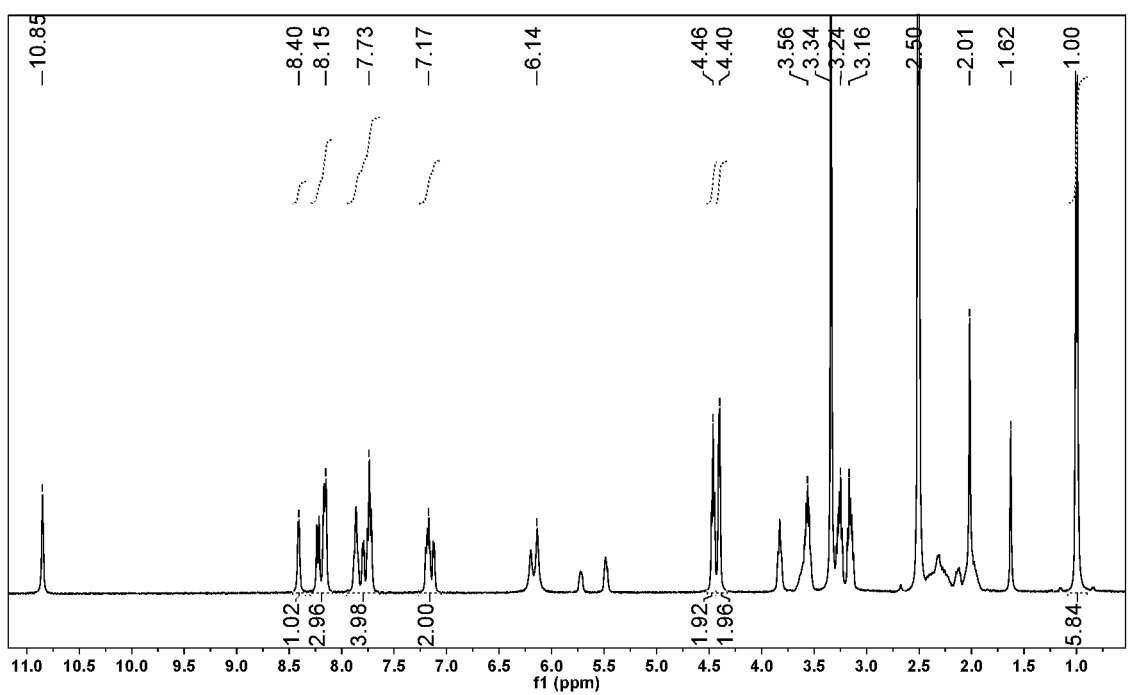
FIG. 20 shows a $^1$H NMR spectrum of (R)-1,2-propanediol solvate Form G in Example 25

Example 25 Preparation of (R)-1,2-propanediol Solvate Form G 51.3 mg of acalabrutinib freebase was weighed into a 1.5-mL glass vial, and 0.5 mL of (R)-1,2-propanediol was added. The mixture was stirred at room temperature overnight. Solids were obtained by isolation. The solid obtained in the present example was confirmed to be (R)-1,2-propanediol solvate Form G. The XRPD pattern is substantially as depicted in FIG. 17, and the XRPD data are listed in Table 28. The DSC curve is substantially as depicted in FIG. 18. The first endotherm peak at around 84° C. corresponds to the desolvating endothermic peak. The TGA curve shows about 10.1% weight loss when heated to 190° C., which is substantially as depicted in FIG. 19. The $^1$H NMR spectrum is depicted in FIG. 20. According to the $^1$H NMR data, one mole of (R)-1,2-propanediol solvate Form G contains about two moles of (R)-1,2-propanediol. (R)-1,2-propanediol has characteristic chemical shift peaks at around 1.00, 3.16, 3.24, 3.56, 4.40 and 4.46.

TABLE 28

| 2θ (±0.2°) | d spacing | Intensity % |
| --- | --- | --- |
| 5.11 | 17.31 | 100.00 |
| 6.62 | 13.35 | 27.17 |
| 7.70 | 11.48 | 10.59 |
| 10.72 | 8.25 | 13.38 |
| 12.15 | 7.28 | 74.10 |
| 13.47 | 6.57 | 65.32 |
| 15.57 | 5.69 | 51.38 |
| 16.97 | 5.22 | 44.26 |
| 17.72 | 5.01 | 34.77 |
| 18.57 | 4.78 | 20.62 |
| 20.64 | 4.30 | 43.04 |
| 21.29 | 4.17 | 28.78 |
| 22.99 | 3.87 | 38.30 |
| 23.71 | 3.75 | 28.27 |
| 25.87 | 3.44 | 20.97 |
| 26.41 | 3.37 | 14.65 |
| 28.98 | 3.08 | 8.43 |

Example 26 Preparation of (R)-1,2-propanediol Solvate Form G 1.22 g of solid was weighed into a 20-mL glass vial and 10.0 mL of (R)-1,2-propanediol was added. The mixture was stirred magnetically at room temperature overnight, 1.12 g of solid was obtained by isolation and drying. The obtained solid was confirmed to be Form G of the present disclosure. The XRPD data are listed in Table 29. Form G of the present example and Form G of Example 25 have identical or similar XRPD patterns, revealing that they are the same crystalline form and possess the same properties.

TABLE 29

| 2θ (0.2°) | d spacing | Intensity % |
| --- | --- | --- |
| 5.24 | 16.88 | 100.00 |
| 6.71 | 13.17 | 19.59 |
| 7.81 | 11.32 | 8.53 |
| 10.76 | 8.22 | 15.55 |
| 12.39 | 7.14 | 84.94 |
| 13.30 | 6.66 | 36.96 |
| 13.64 | 6.49 | 71.90 |
| 15.92 | 5.57 | 66.87 |
| 16.29 | 5.44 | 21.98 |
| 17.24 | 5.14 | 67.05 |
| 17.90 | 4.96 | 41.47 |
| 18.79 | 4.72 | 29.86 |
| 20.38 | 4.36 | 30.57 |
| 20.99 | 4.23 | 55.18 |
| 21.39 | 4.15 | 24.76 |
| 23.15 | 3.84 | 42.69 |
| 23.92 | 3.72 | 22.60 |
| 26.08 | 3.42 | 22.69 |
| 26.66 | 3.34 | 11.15 |
| 27.43 | 3.25 | 10.24 |
| 28.77 | 3.10 | 9.88 |
| 29.23 | 3.05 | 13.60 |

Example 27 Purity of (R)-1,2-propanediol Solvate Form G

HPLC was applied to test the chemical purity of freebase and (R)-1,2-propanediol solvate Form G of the present disclosure, and the purity change was calculated.

HPLC purity test results show that (R)-1,2-propanediol solvate Form G of the present disclosure has substantial purification effect. The purity of freebase is 98.93%, while (R)-1,2-propanediol solvate Form G of the present disclosure has a purity of 99.86% and the purity is increased by 0.93%.

Example 28 Stability of (R)-1,2-propanediol Solvate Form G

Figure 34:
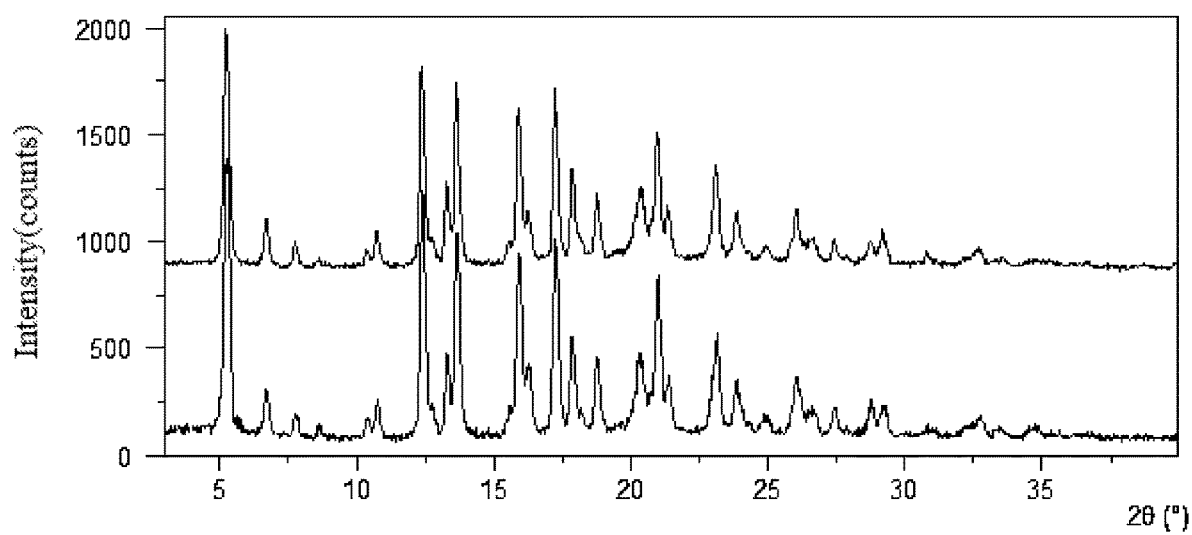
FIG. 34 shows an XRPD pattern overlay of Form G from stability study (from top to bottom: initial, stored at 25° C./60% RH for 2 months in closed dish)

Approximately 10 mg of Form G of the present disclosure was weighed and stored at 25° C./60% RH in closed dish. Crystalline forms were checked by XRPD. The results are shown in Table 30, and the XRPD overlay is shown in FIG. 34.

TABLE 30

| Condition | Storage time | Solid form |
| --- | --- | --- |
| Initial | — | Form G |
| 25° C./60% RH in closed dish | 2 months | Form G |

The results show that Form G kept stable for at least 2 months at 25° C./60% RH in closed dish.

Example 29 Intrinsic Dissolution Rate of (R)-1,2-propanediol Solvate Form G

Figure 35:
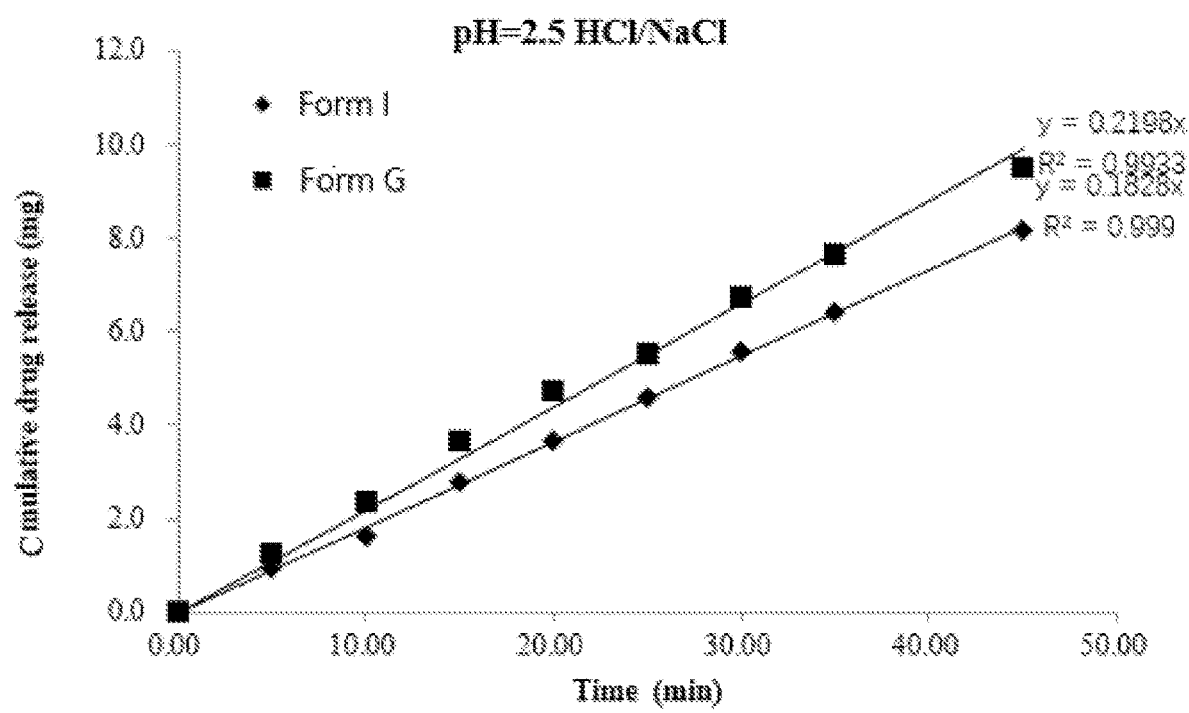
FIG. 35 shows the intrinsic dissolution profile of Form G

Approximately 200 mg of Form G and Form I in WO2017002095A1 were added into the die, compressed at 10 kN and held for 1 minute to obtain a pellet having a surface area of 0.5 cm². The whole tool with the pellet was transferred to a dissolution apparatus to test the intrinsic dissolution. Test conditions are shown in Table 31. Dissolution profile is presented in FIG. 35 and dissolution data are presented in Table 32. The slope (mg/min) was calculated according to the data within 0-45 minutes. Intrinsic dissolution rate (IDR, mg/min/cm²) was further calculated according to the slope. IDR results are presented in Table 33.

TABLE 31

| | |
|---|---|
| Instrument | Agilent 708DS |
| Medium | pH = 2.5 HCl/NaCl aqueous solution |
| Volume | 500 mL |
| Speed | 100 rpm |
| Temperature | 37° C. |
| Sampling Time | 5, 10, 15, 20, 25, 30, 35, 45 min |
| Supplement medium | No (Sampling 1.0 mL at each time point) |

TABLE 32

| Time | Cumulative dissolution (mg) | |
|---|---|---|
| (min) | Form I | Form G |
| 0 | 0.00 | 0.00 |
| 5 | 0.92 | 1.28 |
| 10 | 1.64 | 2.36 |
| 15 | 2.81 | 3.68 |
| 20 | 3.66 | 4.76 |
| 25 | 4.62 | 5.51 |
| 30 | 5.58 | 6.71 |
| 35 | 6.40 | 7.65 |
| 45 | 8.16 | 9.50 |

TABLE 33

| Solid form | IDR (mg/min/cm²) |
|---|---|
| Form I in WO2017002095A1 | 0.3656 |
| Form G | 0.4396 |

The results show that the IDR of Form G is 1.2 times higher than that of Form I in WO2017002095A1.

Example 30 Compressibility of (R)-1,2-propanediol Solvate Form G

Approximately 80 mg of Form G and Form I of WO2017002095A1 were weighed into the dies of a φ6 mm round tooling, compressed at 10 kN manually, and then stored in a desiccator for 24 hours until complete elastic recovery. Radial crushing force (hardness, H)) was tested with an intelligent tablet hardness tester. Diameter (D) and thickness (L) were tested with caliper. Tensile strength of the powder with different hardness was calculated with the following formula: $T=2H/\pi DL$. Under a certain force, the greater the tensile strength, the better the compressibility. The results are presented in Table 34.

TABLE 34

| Solid form | Tensile strength (MPa) |
|---|---|
| Form I in WO2017002095A1 | Unable to be compressed into a tablet |
| Form G | 1.62 |

The results indicate that Form G has higher tensile strength and better compressibility compared with Form I in WO2017002095A1.

Example 31 Adhesiveness of (R)-1,2-propanediol Solvate Form G

Approximately 30 mg of Form G and Form I in WO2017002095A1 were weighed, added into the dies of a φ8 mm round tooling, compressed at 10 kN and held for about 30 s. The amount of material sticking to the punch was weighed. The compression was repeated twice and the cumulative amount and average amount of material sticking to the punch during the compression were recorded. Detailed experimental results are summarized in Table 35.

TABLE 35

| Solid form | Cumulative amount (μg) | Average amount (μg) |
|---|---|---|
| Form I in WO2017002095A1 | 90 | 45 |
| Form G | 60 | 30 |

Test results indicate that the amount sticking to the punch of Form I in WO2017002095A1 is higher than of that of Form G. The adhesiveness of Form G is superior to that of Form I in WO2017002095A1.

Example 32 Flowability of (R)-1,2-propanediol Solvate Form G

Compressibility index or Carr index is usually utilized to evaluate the flowability of powder and granules during the drug product process. Compressibility index test method is as follows: a certain amount of powder was added into a measuring cylinder and bulk volume was recorded. Then the powder was tapped to make it in the tightest state and the tapped volume was recorded. The bulk density ($\rho_0$), tapped density ($\rho_f$) were calculated and compressibility index was calculated according to $c=(\rho_f-\rho_0)/\rho_f$.

Criteria of flowability is shown in Table 36.

TABLE 36

| Compressibility index (%) | Flowability |
|---|---|
| ≤10 | Excellent |
| 11-15 | Good |
| 16-20 | Fair |
| 21-25 | Passable |
| 26-31 | poor |
| 32-37 | Very poor |
| >38 | Very, very poor |

Flowability evaluation results of Form G are presented in Table 37, indicating that Form G has good flowability.

TABLE 37

| Solid form | Bulk density ($\rho_0$, g/mL) | Tapped density ($\rho_f$, g/mL) | Compressibility index (%) | Flowability |
|---|---|---|---|---|
| Form G | 0.443 | 0.488 | 11% | Good |

Example 33 Preparation of (R)-1,2-propanediol Solvate Form CS15

Figure 21:
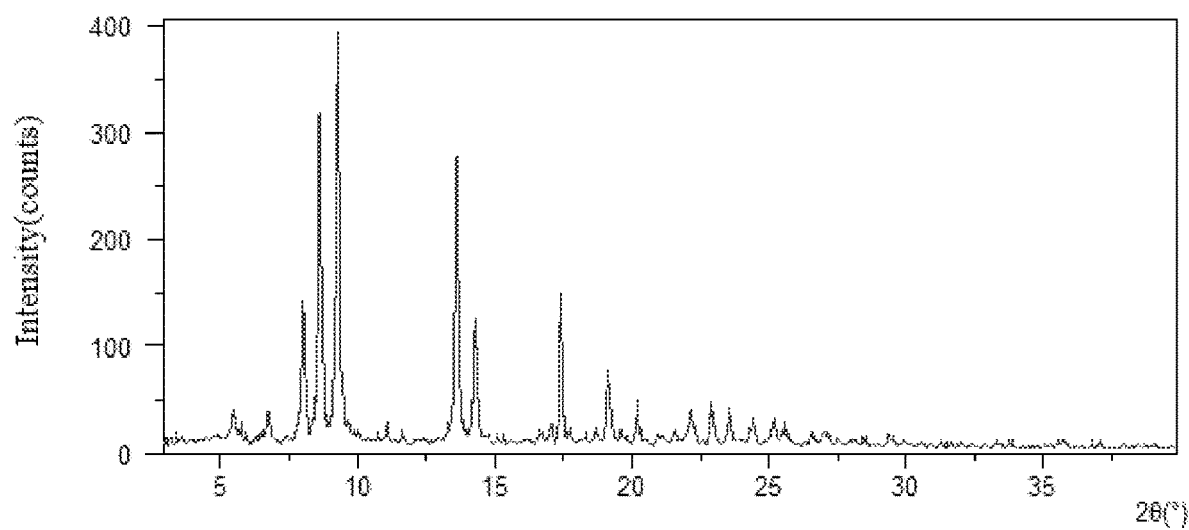
FIG. 21 shows an XRPD pattern of (R)-1,2-propanediol solvate Form CS15 in Example 33

51.3 mg of acalabrutinib free base was weighed into a 1.5-mL glass vial and 0.5 mL of (R)-1,2-propanediol was added. The mixture was stirred at room temperature overnight. Solids were obtained by isolation. 15 mg of obtained solid was suspended into 0.3 mL of acetonitrile, and stirred at −20° C. for 6 days. White crystalline solid was obtained via centrifugal separation. The solid obtained in the present example was confirmed to be Form CS15. The XRPD pattern is substantially as depicted in FIG. 21, and the XRPD data are listed in Table 38.

Figure 24:
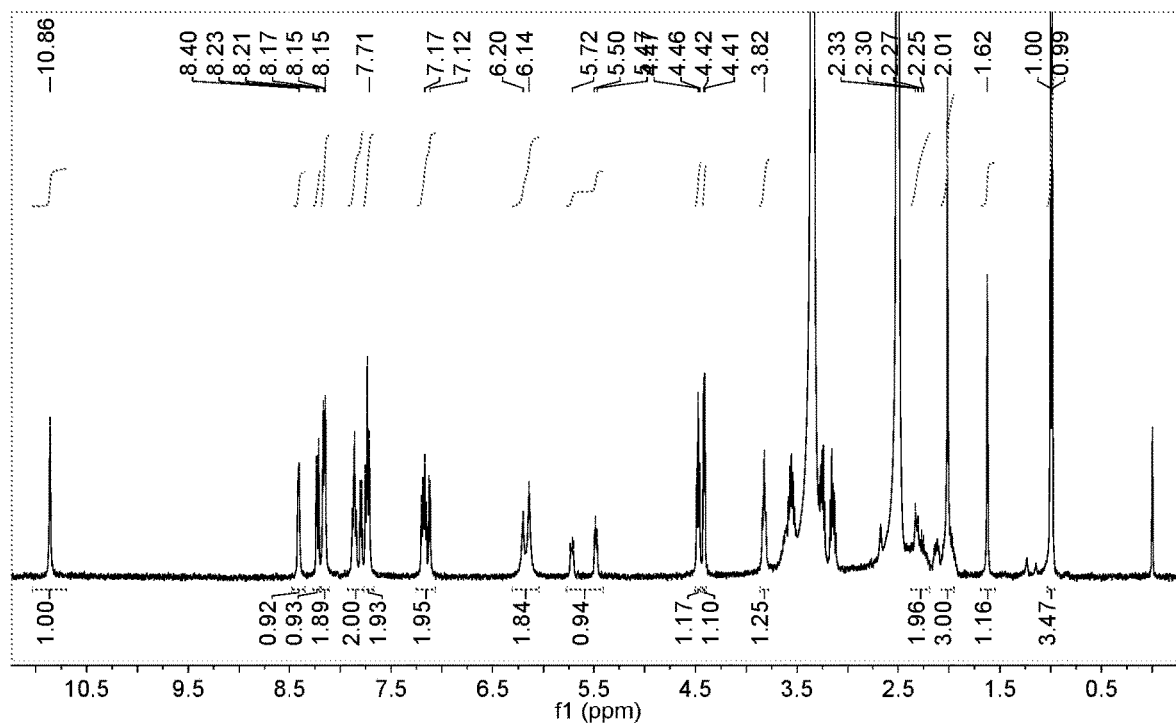
FIG. 24 shows a $^1$H NMR spectrum of (R)-1,2-propanediol solvate Form CS15 in Example 33

$^1$H NMR spectrum is substantially as depicted in FIG. 24 and the characteristic chemical shift peaks is consistent with the compound structure. According to the $^1$H NMR data, one mole (R)-1,2-propanediol solvate Form CS15 contains about one mole of (R)-1,2-propanediol. Detailed $^1$H NMR data are: $^1$H NMR (400 MHz, DMSO) δ10.86 (s, 1H), 8.41 (d, J=4.1 Hz, 1H), 8.22 (d, J=8.3 Hz, 1H), 8.19-8.11 (m, 2H), 7.92-7.77 (m, 1H), 7.73 (t, J=7.7 Hz, 2H), 7.25-7.06 (m, 2H), 6.17 (d, J=23.7 Hz, 2H), 5.78-5.40 (m, 1H), 4.47 (t, J=5.7 Hz, 1H), 4.41 (d, J=4.5 Hz, 1H), 3.82 (s, 1H), 2.29 (dd, J=22.6, 8.9 Hz, 2H), 2.01 (s, 3H), 1.62 (s, 1H), 0.99 (d, J=6.2 Hz, 3H).

TABLE 38

| 2θ (±0.2°) | d spacing | Intensity % |
|---|---|---|
| 5.46 | 16.20 | 5.95 |
| 6.75 | 13.09 | 6.20 |
| 8.03 | 11.01 | 34.24 |
| 8.64 | 10.23 | 81.08 |
| 9.28 | 9.53 | 100.00 |
| 13.61 | 6.51 | 69.55 |
| 14.29 | 6.20 | 30.05 |
| 17.40 | 5.10 | 35.92 |
| 19.16 | 4.63 | 17.45 |
| 20.21 | 4.39 | 7.56 |
| 22.15 | 4.01 | 6.38 |
| 22.92 | 3.88 | 7.71 |
| 23.56 | 3.78 | 8.08 |
| 24.41 | 3.65 | 5.54 |
| 25.35 | 3.51 | 2.09 |

Example 34 Preparation of (R)-1,2-propanediol Solvate Form CS15

785.7 mg of solid was weighed into a 20-mL glass vial and 16.5 mL of (R)-1,2-propanediol/acetonitrile (1:10, v/v) was added. The mixture was stirred magnetically at room temperature overnight. 783.1 mg of solid was obtained by isolation and drying.

Figure 22:
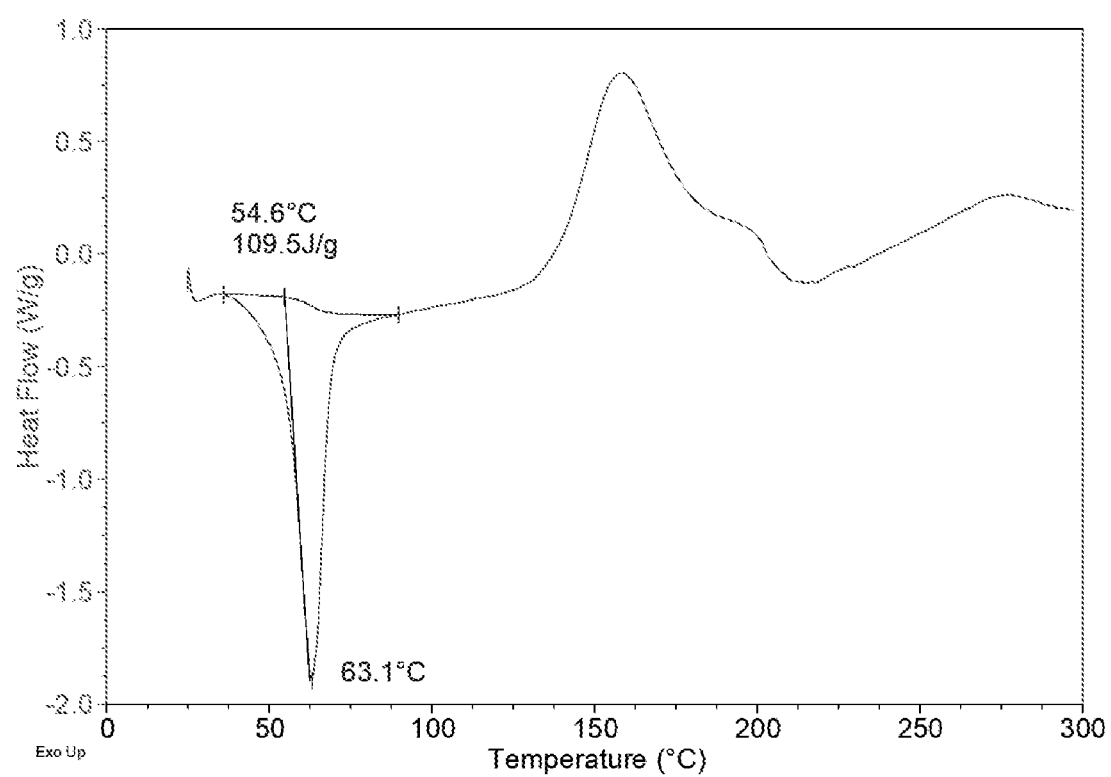
FIG. 22 shows a DSC curve of (R)-1,2-propanediol solvate Form CS15 in Example 34
Figure 23:
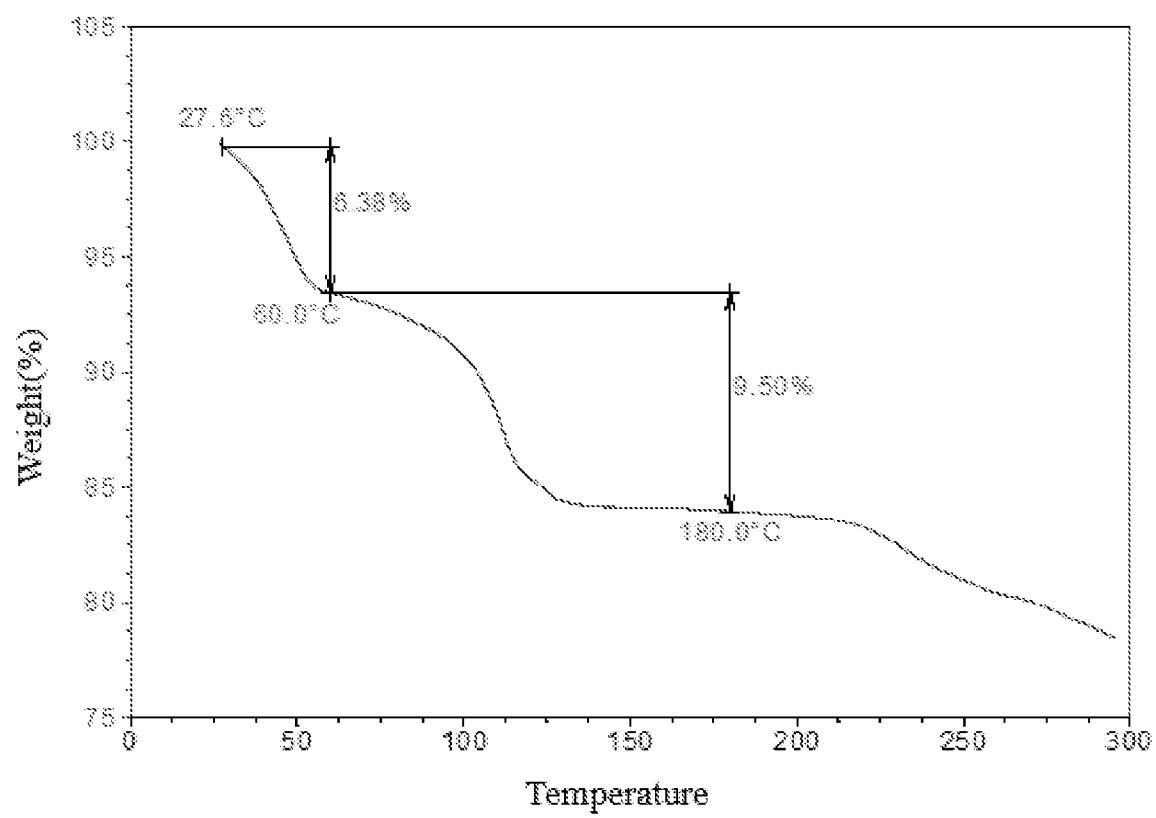
FIG. 23 shows a TGA curve of (R)-1,2-propanediol solvate Form CS15 in Example 34

The solid obtained in the present example was confirmed to be Form CS15. The XRPD data are listed in Table 39 and the DSC curve is substantially as depicted in FIG. 22. The first endothermic peak at around 55° C. corresponds to the desolvating endothermic peak. The TGA curve shows about 15.9% weight loss when heated to 180° C., which is substantially as depicted in FIG. 23.

Form CS15 of the present example and Form CS15 of Example 33 have identical or similar XRPD patterns, revealing that they are the same crystalline form and possess the same properties.

TABLE 39

| 2θ (±0.2°) | d spacing | Intensity % |
|---|---|---|
| 6.75 | 13.10 | 2.86 |
| 8.01 | 11.04 | 18.83 |
| 8.56 | 10.33 | 74.42 |
| 9.18 | 9.63 | 100.00 |
| 13.59 | 6.52 | 35.98 |
| 14.27 | 6.21 | 19.69 |
| 16.73 | 5.30 | 7.18 |
| 17.22 | 5.15 | 62.24 |
| 19.12 | 4.64 | 15.64 |
| 20.02 | 4.44 | 20.19 |
| 21.10 | 4.21 | 5.18 |
| 22.02 | 4.04 | 15.30 |
| 22.90 | 3.88 | 28.75 |
| 23.61 | 3.77 | 20.25 |
| 23.96 | 3.71 | 7.89 |
| 24.29 | 3.66 | 12.85 |
| 25.15 | 3.54 | 22.95 |
| 26.55 | 3.36 | 9.56 |
| 26.93 | 3.31 | 12.72 |
| 28.00 | 3.19 | 4.41 |
| 29.36 | 3.04 | 6.16 |

Example 35 Purity of (R)-1,2-propanediol Solvate Form CS15

HPLC was applied to test the chemical purity of freebase and (R)-1,2-propanediol solvate Form CS15 of the present disclosure, and the purity change was calculated.

HPLC purity test results show that (R)-1,2-propanediol solvate Form CS15 of the present disclosure has substantial purification effect. The purity of freebase is 99.20%, while (R)-1,2-propanediol solvate Form CS15 of the present disclosure has a purity of 99.83% and the purity is increased by 0.63%.

Example 36 Stability of (R)-1,2-propanediol Solvate Form CS15

Figure 36:
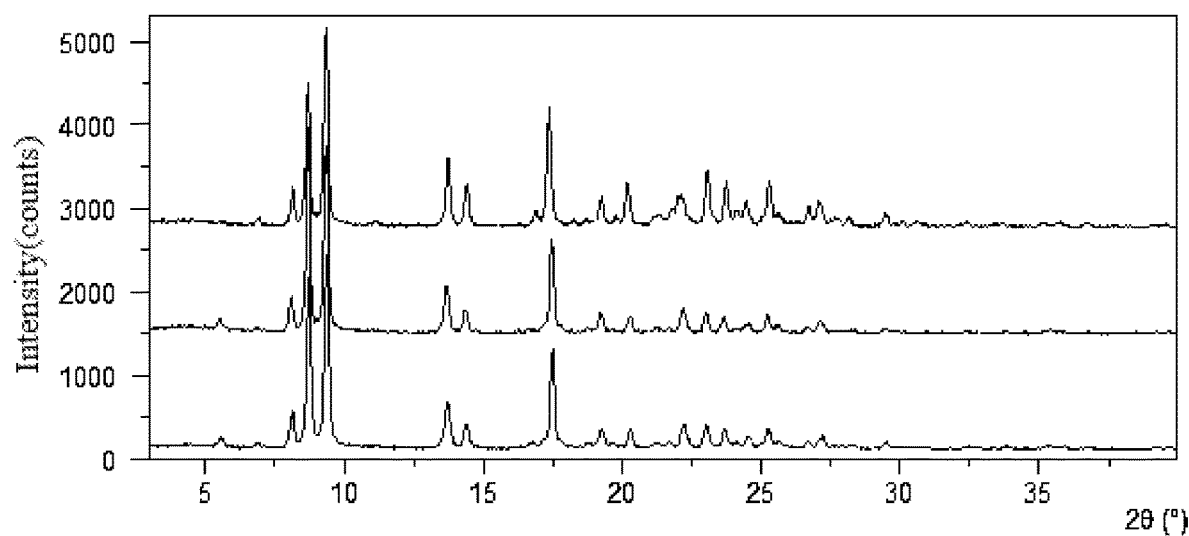
FIG. 36 shows an XRPD pattern overlay of Form CS15 from stability study (from top to bottom: initial, stored at 25° C./60% RH for 2 months in closed dish, stored at 25° C./60% RH for 2 months in open dish)

Approximately 10 mg of Form CS15 of the present disclosure was weighed and stored at different conditions of 25° C./60% RH in open dish, 25° C./60% RH in closed dish. Crystalline forms were checked by XRPD. The results are shown in Table 40, and the XRPD overlay is shown in FIG. 36.

TABLE 40

| Condition | Storage time | Solid form |
|---|---|---|
| Initial | — | Form CS15 |
| 25° C./60% RH in closed dish | 2 months | Form CS15 |
| 25° C./60% RH in open dish | 2 months | Form CS15 |

The results show that Form CS15 kept stable for at least 2 months at 25° C./60% RH in open dish, 25° C./60% RH in closed dish. It shows that Form CS15 has good stability under both long-term and accelerated conditions.

Example 37 Intrinsic Dissolution Rate of (R)-1,2-Propanediol Solvate Form CS15

Figure 37:
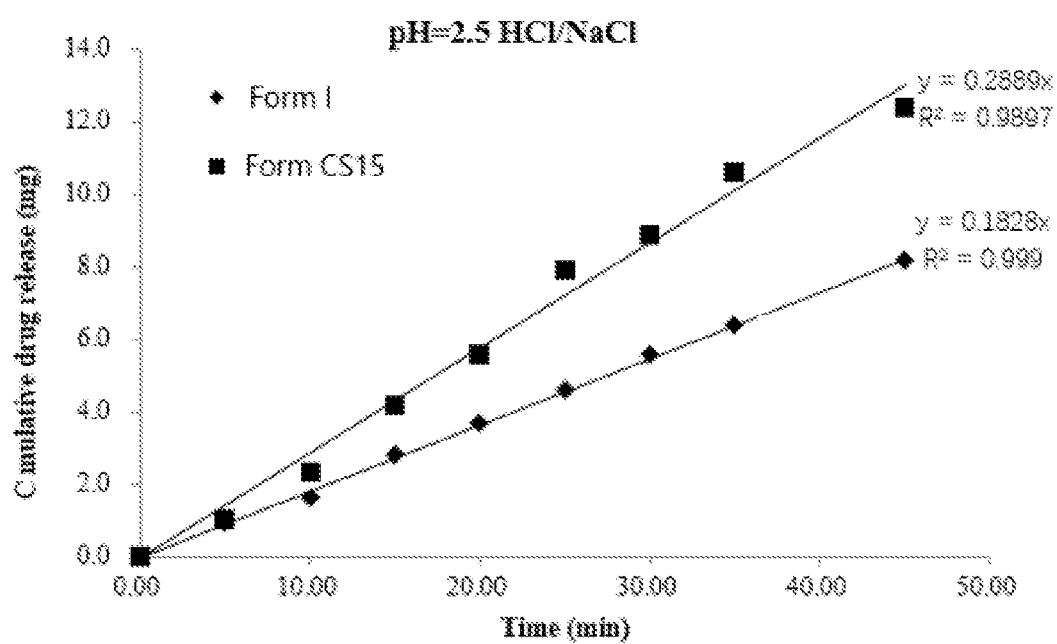
FIG. 37 shows the intrinsic dissolution profile of Form CS15

Approximately 200 mg of Form CS15 and Form I in WO2017002095A1 were added into the die, compressed at 10 kN and held for 1 minute to obtain a pellet having a surface area of 0.5 cm$^2$. The whole tool with the pellet was transferred to a dissolution apparatus to test the intrinsic dissolution. Dissolution method is shown in Table 41. Dissolution profile is presented in FIG. 37 and dissolution data are presented in Table 42. The slope (mg/min) was calculated according to the data within 0-45 minutes. Intrinsic dissolution rate (IDR, mg/min/cm$^2$) was further calculated according to the slope. IDR results are presented in Table 43.

TABLE 41

| Instrument | Agilent 708DS |
|---|---|
| Medium | pH = 2.5 HCl/NaCl aqueous solution |
| Volume | 500 mL |
| Speed | 100 rpm |
| Temperature | 37° C. |
| Sampling Time | 5, 10, 15, 20, 25, 30, 35, 45 min |
| Supplement medium | No (Sampling 1.0 mL at each time point) |

TABLE 42

| Time | Cumulative dissolution (mg) | |
|---|---|---|
| (min) | Form I | Form CS15 |
| 0 | 0.00 | 0.00 |
| 5 | 0.92 | 1.06 |
| 10 | 1.64 | 2.34 |
| 15 | 2.81 | 4.20 |
| 20 | 3.66 | 5.60 |
| 25 | 4.62 | 7.89 |
| 30 | 5.58 | 8.86 |
| 35 | 6.40 | 10.60 |
| 45 | 8.16 | 12.41 |

TABLE 43

| Solid form | IDR (mg/min/cm$^2$) |
|---|---|
| Form I in WO2017002095A1 | 0.3656 |
| Form CS15 | 0.5778 |

The results show that the IDR of Form CS15 is 1.6 times higher than that of Form I in WO2017002095A1.

Example 38 Hygroscopicity of (R)-1,2-propanediol Solvate Form CS15

Figure 38:
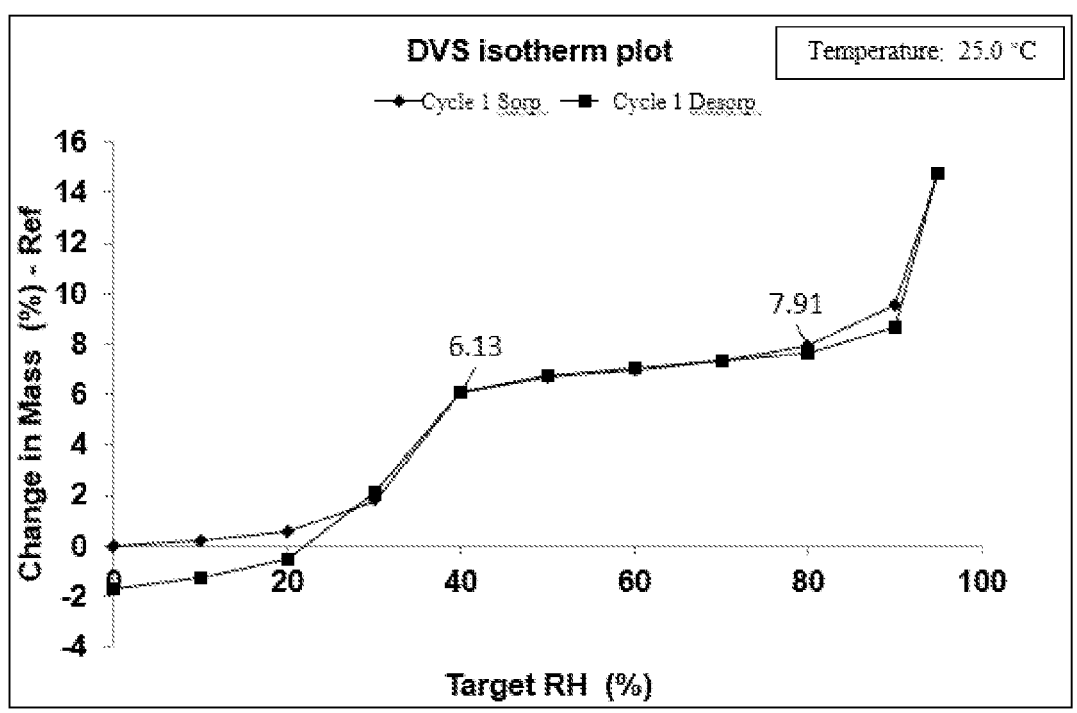
FIG. 38 shows a DVS plot of Form CS15
Figure 39:
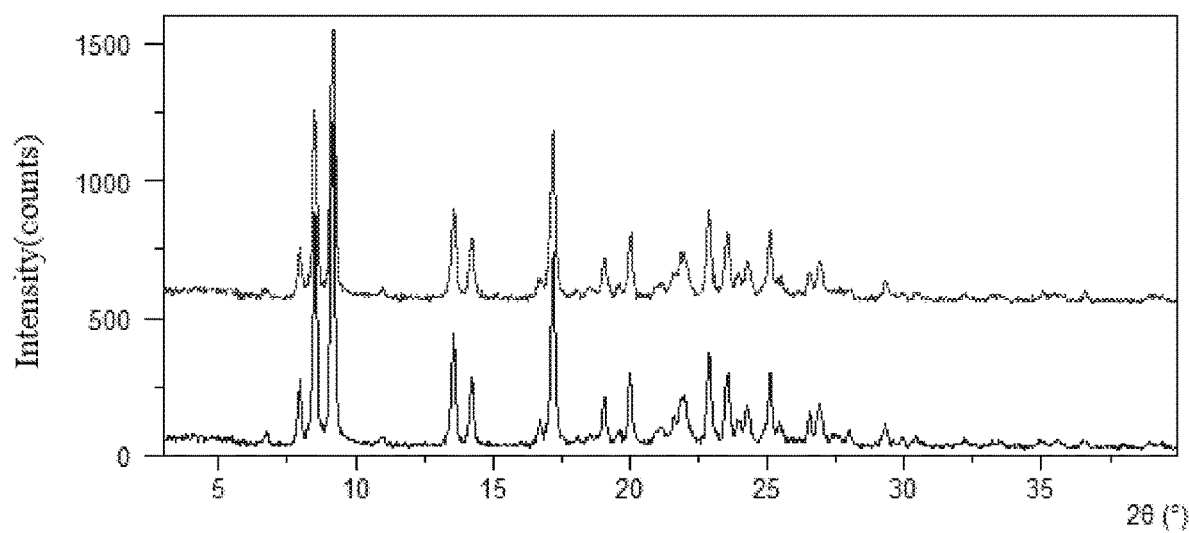
FIG. 39 shows an XRPD pattern overlay of Form CS15 before and after DVS test (bottom: before DVS; top: after DVS)

Dynamic vapor sorption (DVS) was applied to test hygroscopicity of Form CS15 with about 10 mg of sample. Weight changes at each relative humidity were recorded in a cycle of 0-95%-0 RH at 25° C.±1° C. DVS plot is substantially as depicted in FIG. 38, and XRPD patterns before and after DVS are compared in FIG. 39.

Description and definition of hygroscopicity (general notice 9103 drug hygroscopicity test guidelines in 2015 edition of Chinese Pharmacopoeia, test at 25° C.+/−1° C., 80% RH).

deliquescent: Sufficient water is absorbed to form a liquid;
very hygroscopic: Increase in mass is equal to or greater than 15 percent;
hygroscopic: Increase in mass is less than 15 percent and equal to or greater than 2 percent;
slightly hygroscopic: Increase in mass is less than 2 percent and equal to or greater than 0.2 percent.
non hygroscopic or almost non hygroscopic: Increase in mass is less than 0.2%.

The results show that Form CS15 is slightly hygroscopic with a weight gain of 1.78% at 80% RH.

Example 39 Compressibility of (R)-1,2-propanediol Solvate Form CS15

Approximately 80 mg of Form CS15 and Form I in WO2017002095A1 were weighed into the dies of a φ6 mm round tooling, compressed at 10 kN manually, and then stored in a desiccator for 24 hours until complete elastic recovery. Radial crushing force (hardness, H) was tested with an intelligent tablet hardness tester. Diameter (D) and thickness (L) were tested with caliper. Tensile strength of the powder with different hardness was calculated with the following formula: T=2H/πDL. Under a certain force, the greater the tensile strength, the better the compressibility. The results are presented in Table 44.

TABLE 44

| Solid form | Tensile strength (MPa) |
|---|---|
| Form I in WO2017002095A1 | Unable to be compressed into a tablet |
| Form CS15 | 1.18 |

The results indicate that Form CS15 has higher tensile strength and better compressibility compared with Form I in WO2017002095A1.

Figure 5:
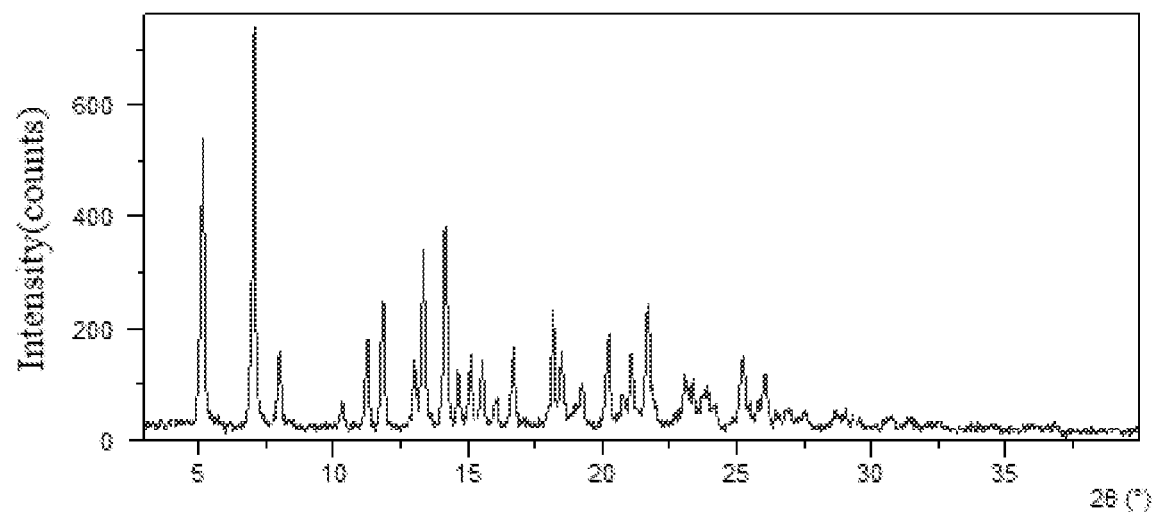
FIG. 5 shows an XRPD pattern of ethylene glycol solvate Form B in Example 40
Figure 6:
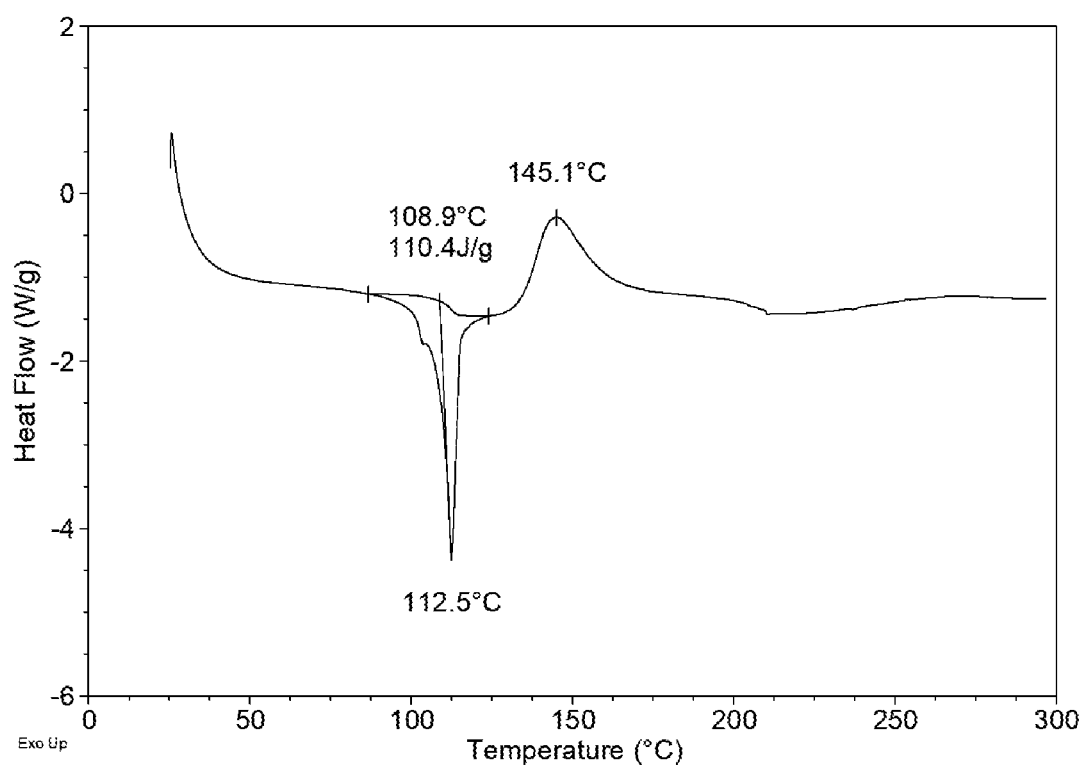
FIG. 6 shows a DSC curve of ethylene glycol solvate Form B in Example 40
Figure 7:
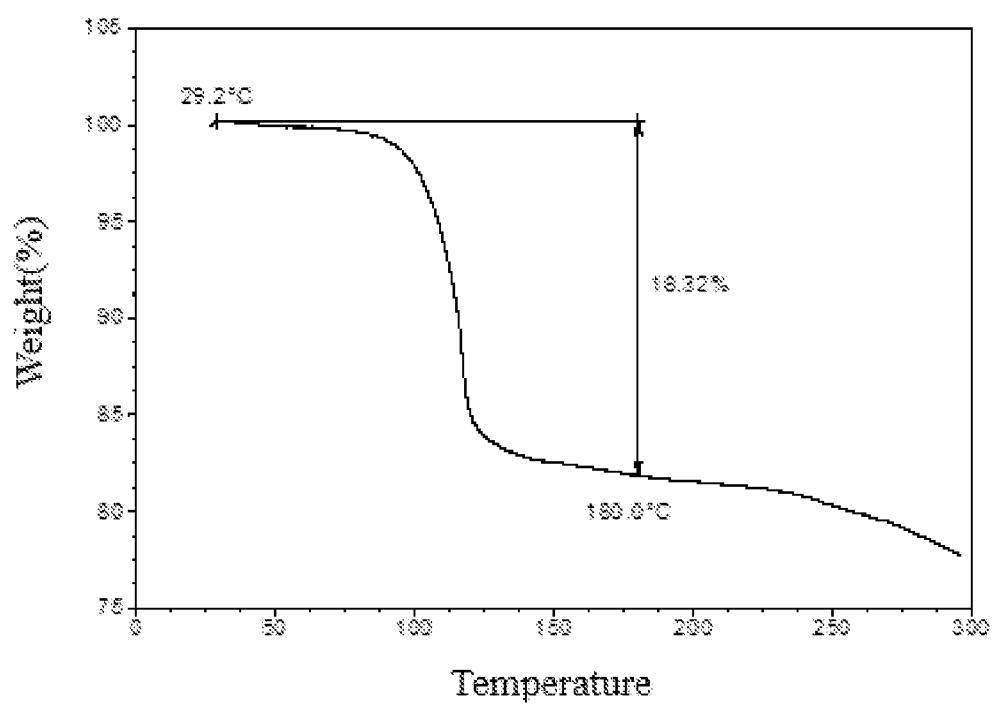
FIG. 7 shows a TGA curve of ethylene glycol solvate Form B in Example 40

Example 40 Preparation of Ethylene Glycol Solvate Form B 14.3 mg of acalabrutinib free base was weighed into a 3-mL glass vial and 0.5 mL of ethylene glycol was added to make a clear solution. The uncapped 3-mL glass vial was placed in a closed 20-mL glass vial with 3 mL of IPAc. The ethylene glycol solution was exposed to IPAc vapor at room temperature for 3 days. The solid was obtained by isolation. The solid obtained in the present example was confirmed to be ethylene glycol solvate Form B. The XRPD pattern is substantially as depicted in FIG. 5, and the XRPD data are listed in Table 45. The DSC curve is substantially as depicted in FIG. 6. The first endothermic peak at around 109° C. corresponds to the desolvating endothermic peak. The TGA curve shows about 18.3% weight loss when heated to 180° C., which is substantially as depicted in FIG. 7.

Figure 8:
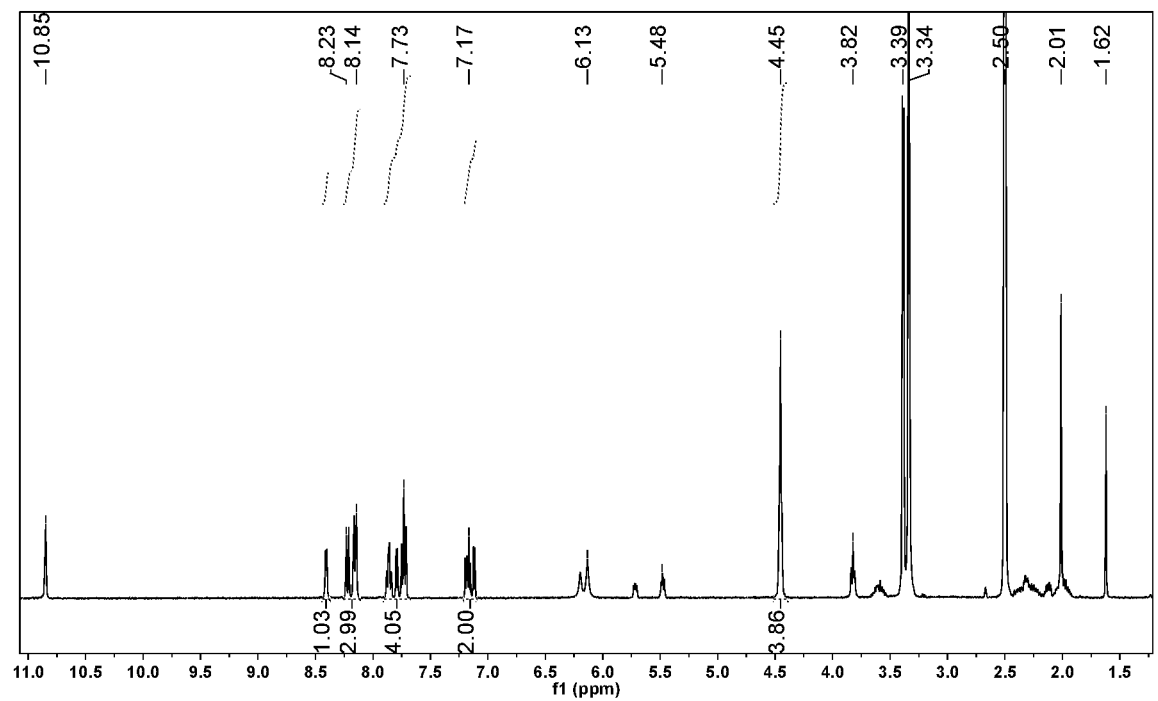
FIG. 8 shows a $^1$H NMR spectrum of ethylene glycol solvate Form B in Example 40

The $^1$H NMR spectrum is depicted in FIG. 8. According to the $^1$H NMR data, one mole of ethylene glycol solvate Form B contains about two moles of ethylene glycol. Ethylene glycol has characteristic chemical shift peaks at around 3.39 and 4.45.

TABLE 45

| 2θ (±0.2°) | d spacing | Intensity % |
|---|---|---|
| 5.14 | 17.18 | 71.66 |
| 7.06 | 12.52 | 100.00 |
| 8.01 | 11.04 | 20.33 |
| 10.32 | 8.57 | 5.55 |
| 11.26 | 7.86 | 21.71 |
| 11.82 | 7.49 | 29.32 |
| 13.01 | 6.80 | 15.73 |
| 13.32 | 6.65 | 44.55 |
| 14.14 | 6.26 | 49.92 |
| 14.65 | 6.05 | 13.55 |
| 15.08 | 5.87 | 15.37 |
| 15.52 | 5.71 | 15.23 |

TABLE 45-continued

| 2θ (±0.2°) | d spacing | Intensity % |
|---|---|---|
| 16.06 | 5.52 | 6.79 |
| 16.68 | 5.32 | 17.72 |
| 18.14 | 4.89 | 27.46 |
| 18.48 | 4.80 | 16.69 |
| 19.22 | 4.62 | 9.74 |
| 20.21 | 4.39 | 19.34 |
| 21.06 | 4.22 | 17.57 |
| 21.64 | 4.11 | 28.96 |
| 23.09 | 3.85 | 10.35 |
| 25.21 | 3.53 | 15.79 |
| 26.05 | 3.42 | 10.91 |

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

The invention claimed is:

1. An ethyl L-lactate solvate crystalline form A of acalabrutinib,

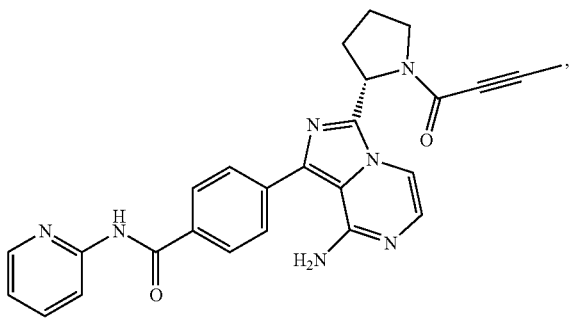 [SMILES: CC#CC(=O)N1CCC[C@H]1c1nc(-c2ccc(C(=O)Nc3ccccn3)cc2)c2c(N)nccn12]

wherein the X-ray powder diffraction pattern shows characteristic peaks at 2theta values of 5.7°±0.2°, 17.4°±0.2° and 18.2°±0.2° using CuKα radiation.

2. The ethyl L-lactate solvate crystalline form A of acalabrutinib according to claim 1, wherein the X-ray powder diffraction pattern shows one or two or three characteristic peaks at 2theta values of 8.5°±0.2°, 13.9°±0.2° and 24.8°±0.2° using CuKα radiation.

3. The ethyl L-lactate solvate crystalline form A of acalabrutinib according to claim 1, wherein the X-ray powder diffraction pattern shows one or two or three characteristic peaks at 2theta values of 19.2°±0.2°, 22.9°±0.2° and 15.1°±0.2° using CuKα radiation.

4. A process for preparing ethyl L-lactate solvate crystalline form A of acalabrutinib according to claim 1, wherein the process comprises:
suspending acalabrutinib free base in ethyl L-lactate or a solvent containing ethyl L-lactate, reacting for 1-3 days at 5-60° C. to obtain a solid.

5. A glycerol solvate crystalline form D of acalabrutinib,

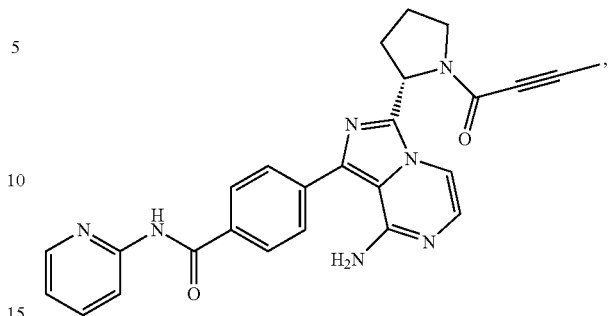

wherein the X-ray powder diffraction pattern shows characteristic peaks at 2theta values of 14.2°±0.2°, 6.7°±0.2° and 13.4°±0.2° using CuKα radiation.

6. The glycerol solvate crystalline form D of acalabrutinib according to claim 5, wherein the X-ray powder diffraction pattern shows one or two or three characteristic peaks at 2theta values of 16.2°±0.2°, 11.0°±0.2° and 9.6°±0.2° using CuKα radiation.

7. The glycerol solvate crystalline form D of acalabrutinib according to claim 5, wherein the X-ray powder diffraction pattern shows one or two or three characteristic peaks at 2theta values of 8.1°±0.2°, 24.3°±0.2° and 20.3°±0.2° using CuKα radiation.

8. A process for preparing glycerol solvate crystalline form D of acalabrutinib according to claim 5, wherein the process comprises:
suspending acalabrutinib free base in glycerol or a solvent containing glycerol, then reacting for 10-72 hours at 20-80° C. to obtain a solid.

9. A pharmaceutical composition, said pharmaceutical composition comprises a therapeutically effective amount of ethyl L-lactate solvate crystalline form A of acalabrutinib according to claim 1, and a pharmaceutically acceptable carrier, a diluent or an excipient.

10. A method of treating mantle cell lymphoma, comprising administering to a subject in need thereof a therapeutically effective amount of ethyl L-lactate solvate crystalline form A of acalabrutinib according to claim 1.

11. A pharmaceutical composition, said pharmaceutical composition comprises a therapeutically effective amount of glycerol solvate crystalline form D of acalabrutinib according to claim 5, and a pharmaceutically acceptable carrier, a diluent or an excipient.

12. A method of treating mantle cell lymphoma, comprising administering to a subject in need thereof a therapeutically effective amount of glycerol solvate crystalline form D of acalabrutinib according to claim 5.

13. The ethyl L-lactate solvate crystalline form A of acalabrutinib according to claim 2, wherein the X-ray powder diffraction pattern shows one or two or three characteristic peaks at 2theta values of 19.2°±0.2°, 22.9°±0.2° and 15.1°±0.2° using CuKα radiation.

14. The glycerol solvate crystalline form D of acalabrutinib according to claim 6, wherein the X-ray powder diffraction pattern shows one or two or three characteristic peaks at 2theta values of 8.1°±0.2°, 24.3°±0.2° and 20.3°±0.2° using CuKα radiation.

* * * * *